(12) United States Patent
Smit et al.

(10) Patent No.: US 12,115,234 B2
(45) Date of Patent: Oct. 15, 2024

(54) METHOD OF PREPARING A COSMETIC COMPONENT

(71) Applicant: THE STELLENBOSCH NANOFIBER COMPANY (PTY) LTD, Montague Gardens (ZA)

(72) Inventors: Anton Eugene Smit, Montague Gardens (ZA); Haydn Kriel, Montague Gardens (ZA); Megan Patricia Coates, Montague Gardens (XK); Justin Stone, Montague Gardens (ZA)

(73) Assignee: THE STELLENBOSCH NANOFIBER COMPANY (PTY) LTD, Montague Gardens (ZA)

( * ) Notice: Subject to any disclaimer, the term of this patent is extended or adjusted under 35 U.S.C. 154(b) by 387 days.

(21) Appl. No.: 17/767,194

(22) PCT Filed: Oct. 7, 2019

(86) PCT No.: PCT/IB2019/058519
§ 371 (c)(1),
(2) Date: Apr. 7, 2022

(87) PCT Pub. No.: WO2021/069952
PCT Pub. Date: Apr. 15, 2021

(65) Prior Publication Data
US 2022/0370304 A1    Nov. 24, 2022

(51) Int. Cl.
| A61K 8/02 | (2006.01) |
| A61K 8/73 | (2006.01) |
| A61K 8/81 | (2006.01) |
| A61Q 19/10 | (2006.01) |

(52) U.S. Cl.
CPC .............. *A61K 8/0212* (2013.01); *A61K 8/73* (2013.01); *A61K 8/735* (2013.01); *A61K 8/8111* (2013.01); *A61Q 19/10* (2013.01); *A61K 2800/28* (2013.01)

(58) Field of Classification Search
CPC ........................ A61K 8/0212; A61K 8/0208
See application file for complete search history.

(56) References Cited

U.S. PATENT DOCUMENTS

| 2010/0307119 A1 | 12/2010 | Leung et al. |
| 2013/0338790 A1 | 12/2013 | Okimura et al. |
| 2016/0369936 A1 | 12/2016 | Hwang |
| 2017/0340090 A1* | 11/2017 | Kim .................. A61K 8/19 |

FOREIGN PATENT DOCUMENTS

| CN | 103784332 A | 5/2014 | |
| CN | 108905643 A | 11/2018 | |
| EP | 1764136 B1 * | 1/2009 | ........... A41D 31/145 |
| JP | 2008179629 A | 8/2008 | |
| JP | 2013136550 A1 | 11/2013 | |
| JP | 2015044327 A | 3/2015 | |
| KR | 101567471 B1 * | 11/2015 | ........... A61K 8/0212 |
| KR | 20170089427 A | 8/2017 | |
| WO | 2015074631 A1 | 5/2015 | |

OTHER PUBLICATIONS

International Search Report and Written Opinion for PCT/IB2019/058519, mailed Jul. 14, 2020 (11 pages).
Database WPI, Week 201764, Thomson Scientific, London, GB; AN 2017-55188C XP002799277 (2 pages).
Database WPI, Week 201521 Thomson Scientific, London, GB; AN 2015-20684K XP002799278 (2 pages).
Database WPI, Week 201348, Thomson Scientific, London, GB; AN 2013-L72209 XP002799279 (2 pages).
Database WPI, week 201910, Thomson Scientific, London GB, AN 2018-98568T XP002799280 (2 pages).
Database WPI, Week 201446, Thomson Scientific, London, GB; AN 2014-N06066, XP002799281 (1 page).

* cited by examiner

*Primary Examiner* — Gina C Justice
(74) *Attorney, Agent, or Firm* — Quarles & Brady, LLP

(57) ABSTRACT

A method for preparing a cosmetic component is provided which includes applying a layer of a dry cosmetic ingredient between a pair of fibrous sheets obtained by electrospinning one or more polymeric materials at least one of which is capable of cold flow under pressure. Sufficient pressure is then applied to the layers of fibrous sheets to cause cold flow of at least some of the polymeric material such that at least parts of the fibrous sheets bond with each other and entrap the cosmetic ingredient in position between them and prevent it from migrating between the sheets during further processing or handling.

15 Claims, 12 Drawing Sheets

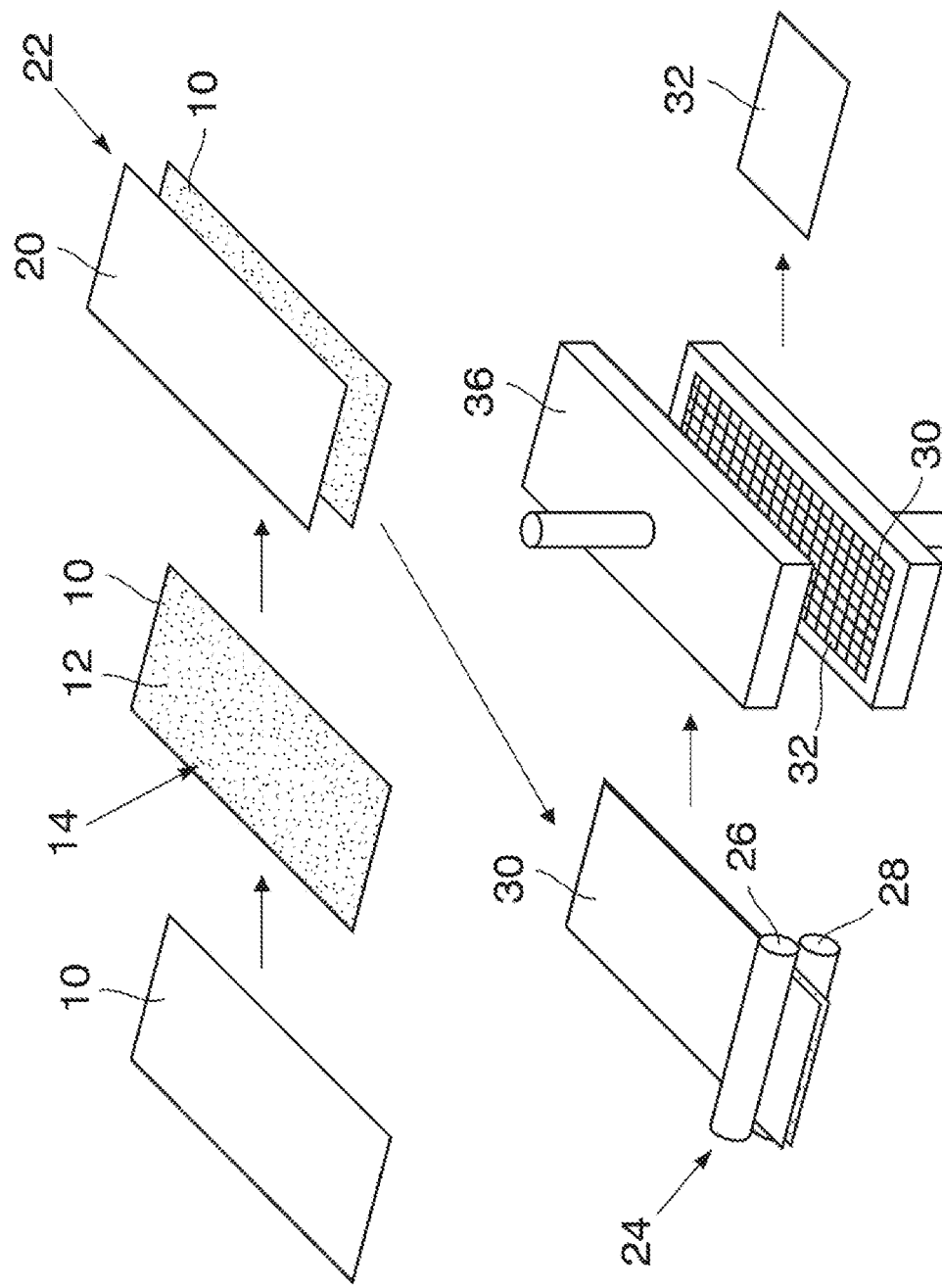

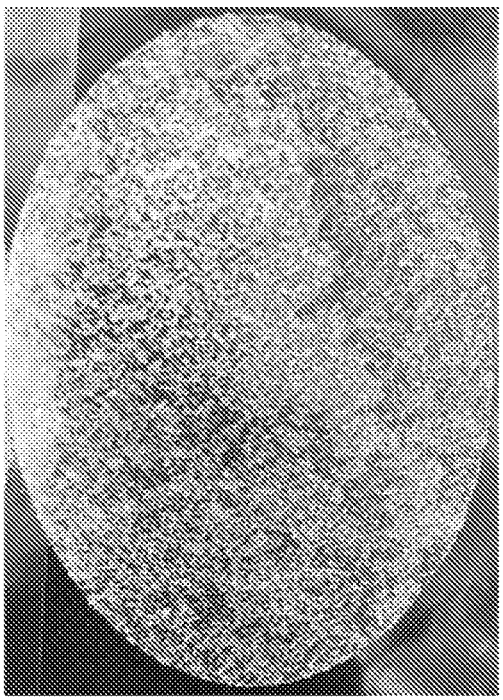
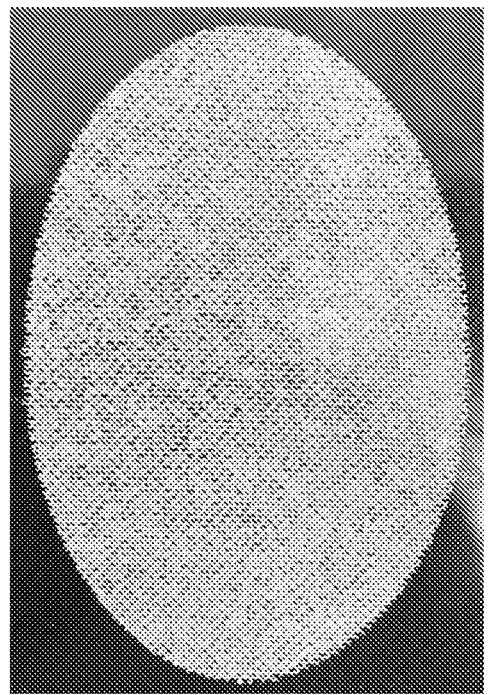
Figure 11                                      Figure 12
Figure 13

METHOD OF PREPARING A COSMETIC COMPONENT

CROSS REFERENCES TO RELATED APPLICATIONS

This is a U.S. National Stage application, filed pursuant to 35 U.S.C. § 371, of international application no. PCT/IB2019/058519, filed on Oct. 7, 2019, the contents of which is incorporated herein by reference in its entirety.

FIELD OF THE INVENTION

This invention relates to a method of preparing a cosmetic component, more particularly to a method of preparing a cosmetic component having more than one layer, each including one or more materials which includes nanofibers obtained by electrospinning, with a dry cosmetic ingredient distributed between the layers.

BACKGROUND TO THE INVENTION

Nanofibers have garnered much attention as carriers of cosmetic active ingredients. This is in part due to the ability to encapsulate active ingredients within the structure of the nanofibers, both within the fibers themselves as well as between the interstices of the fibers. A number of different methods for encapsulating active ingredients exist.

JP 2007335525 discusses three different methods for adding active ingredients directly into nanofibers for cosmetics. 1) The actives are added directly into the polymer solution prior to electrospinning. 2) Cosmetic actives are sprayed onto the nanofibers during electrospinning. 3) Nanofibers are immersed into a solution of dissolved cosmetic actives then removed to dry. These methods are limited in the amount of active ingredients that get incorporated into the nanofibers and also offer little control of dosage or distribution uniformity of active ingredients.

US 2012/14001559 discusses spraying bone material onto biocompatible fiber onto the nanofiber mat, either while simultaneously electrospinning, or by stopping spinning, adding bone material, then starting spinning again. The difficulty in controlling the dose per surface area of the active and long production times are two of the major drawbacks of these methods.

WO 2015/074631 discusses welding nanofibers together and to substrates to manufacture voluminous "tea-bag" form pads of hyaluronic acid (HA)/polyethylene oxide (PEO) nanofibers. By its nature, the structure described through being welded on its circumference to make the "tea-bag" or pad structure does not allow for restriction of movement of the additive within the structure, such that the additives may freely move between the two nanofiber layers to create non-uniform dispersion of actives. This patent application also teaches that pressure and thermal welding or a combination thereof are used for creating strengthened edges of voluminous nanofibrous materials, for creating a fixed joint of two or more nanofiber layers, and for patterning (Example 6). It further teaches that the addition of solid active material between the two nanofibrous layers should be done in such a way that it falls within the welding area so that the active does not inhibit the welding due to the presence of a fill between the nanofibrous layers (Example 8). This teaching is to be expected due to the fact that heat or solvent used in heat or solvent welding will generally degrade, denature or distort the solid active material and render it inactive or even harmful, and the assumption that the solid active will prevent adequate bonding of the nanofiber layers.

All of the methods mentioned above are limited by the compatibility (solubility/temperature/time sensitivity) of the active ingredients, are difficult to control loading dosage of active, or limit the amount of active ingredients that can be loaded into the nanofibers. The methods above are also limited in the case of welding. Welds can only occur in areas where there are no actives and loading and welding have thus to be carefully controlled.

US 2010/0307119 describes electrospinning nanofibers onto one or both sides of substrate medium to prepare a multilayer filter structure. In order to prepare the laminate unit mentioned they electrospun directly onto the substrate using a build-up method, or by vacuum drying a liquid suspension of substrate and nanofibers. In both instances mechanical pressure and adhesive was required to create the laminate structure. Furthermore, this patent application results in a rigid format structure, using a substrate to support the delicate nanofibers.

The present invention serves to mitigate these shortcomings in the prior art by proposing a method for loading greater active:carrier ratio controlled doses of active ingredients within a consolidated nanofiber structure.

The preceding discussion of the background to the invention is intended only to facilitate an understanding of the present invention. It should be appreciated that the discussion is not an acknowledgment or admission that any of the material referred to was part of the common general knowledge in the art as on the priority date of the application.

SUMMARY OF THE INVENTION

In accordance with this invention there is provided a method for preparing a cosmetic component including the steps of:
  applying a layer of a dry cosmetic ingredient between a pair of fibrous sheets obtained by electrospinning one or more polymeric materials at least one of which is capable of cold flow under pressure, and
  subjecting the layers of fibrous sheets to sufficient pressure over the surface of the sheets to cause cold flow of at least some of the polymeric material such that at least parts of the fibrous sheets bond with each other and entrap the cosmetic ingredient in position between them.

The method further includes applying the layer of a dry cosmetic ingredient uniformly between the fibrous sheets; for pressure to be applied in a patterned arrangement over the surface of the fibrous sheets to form a plurality of pockets in which the cosmetic ingredient is trapped and which prevent substantial migration of the cosmetic ingredients during further processing or handling; alternatively for pressure to be applied to the entire surface of the fibrous sheets.

The polymeric material of the fibrous sheets may be selected from thermoplastic polymers, or polymer blends containing thermoplastic polymers with an amorphous component that can be deformed, and may include, but not be limited to, polyethylene oxide (PEO), polyethylene glycol (PEG), polyvinyl acetate (PVAc), polylactic acid (PLA), polycaprolactone (PCL), polyethylene terephthalate (PET), polypropylene (PP), polyvinyl chloride (PVC), polyvinylidene fluoride or polyvinylidene difluoride (PVDF), and Nylon.

The polymeric material of the fibrous sheets may in particular be selected from water soluble thermoplastic polymers, or polymer blends containing thermoplastic polymers with an amorphous component that can be deformed, and may include, but not be limited to, polyethylene oxide (PEO), polyvinyl pyrrolidone (PVP), polyethylene glycol (PEG), polyvinyl acetate (PVAc) and polyvinyl alcohol (PVOH). These may be used in blends where desired and in combination with other water soluble polymers that do not serve as the primary agents for cold flow, including natural polymers such as Pullulan, Sodium Hyaluronate, Dextran or similar sugars, Gelatin or Collagen or similar peptides, Starch or other polysaccharides, Sodium Alginate or synthetic water dispersible polymers such as water soluble polyacrylic/acrylate/acrylamide copolymers and their derivatives/copolymers.

The method still further provides for the cosmetic component to be cut or removed from a larger panel of material.

The method may include laying down a first or lowermost fibrous sheet, applying the dry cosmetic component to the uppermost surface of the first fibrous sheet, laying a second or uppermost fibrous sheet on top of the first sheet with the dry cosmetic component therebetween, and subjecting the layers of fibrous sheets to sufficient pressure to cause at least parts of the fibrous sheets to bond with each other and entrap the cosmetic ingredient in position between them. The cosmetic component may subsequently be removed from the laminated sheets by cutting, punching or the like. The cosmetic component may also be removed from the sheets by a cutting die while pressure is being applied to them. The cosmetic component may be further processed or packaged.

Pressure may be applied to the fibrous sheets by a roller press, stamp press, plate press or the like.

The ambient temperature during the process may be maintained between 1° C. to 35° C., or 5° C. to 30° C., or 10° C. to 30° C., or 15° C. to 30° C., or 15° C. to 25° C., or 16° C. to 25° C., or room temperature.

It is preferred that no heat be applied while the fibrous sheets are subjected to pressure.

Either or both of the fibrous sheets may be carried on a backing or substrate, and the backing may be removed after pressing or remain on or with the cosmetic component. The backing may be a flat sheet of material or may have a mesh or woven construction.

At least one of the fibrous sheets obtained by electrospinning may be made of fiber forming components that are water soluble or otherwise soluble in formulations that have water in them.

The dry cosmetic ingredients may be in a processable format including but not limited to powder, particle, flake, fiber or similar.

The dry cosmetic ingredients may be selected to be in a size range that will not result in large holes cut through fiber sheets when pressure is applied and compression resistance range that permits yielding under direct pressure.

The dry cosmetic ingredients may be of the cosmetic category of ingredients that includes, but is not limited to, the following, including any possible combination of mixtures thereof, beneficial active microbial species, beneficial inactive microbial species, microbial peptides, exfoliant/abrasive particles, cosmetically active ingredients, absorbent, cosmetic pigments, odour reducing ingredients and sun protection ingredients.

The fibrous sheet, obtained by electrospinning, may have an average fiber diameter and fiber diameter distribution, and an area density suitable to entrap the dry cosmetic actives, based on the particle sizes, such that they do not noticeably fall through the structure.

The fibrous sheet may dissolve in contact with a wet medium with water as one of its constituents, to release the dry cosmetic ingredients.

At least one fibrous sheet may contain additional cosmetic ingredients in the fibers that are released as the fibers dissolve in contact with a wet medium. Such additional cosmetic ingredients may include antioxidants, emollients, humectants, actives, surfactants or preservatives. Such additional cosmetic may further be selected to provide adhesion to skin.

The cosmetic component may be further impregnated with cosmetic liquids, containing cosmetically active ingredients including a surfactant or emulsifier that will not dissolve or significantly distort or shrink the fibers.

The cosmetic component may be converted into a cosmetic relevant format to apply to the skin including but not limited to a patch, full facial mask, split facial mask and a roll.

A cosmetic component which includes two layers of fibrous sheets obtained by electrospinning one or more polymeric materials with a dry cosmetic component between the layers, characterised in that the layers are secured together in at least one area of bonding created through cold flow of at least some of the polymeric material, which area includes the dry cosmetic component.

The at least one area of bonding may extend over the entire surface of the cosmetic component; alternatively a plurality of areas of bonding may extend over the surface of the cosmetic component, the plurality of areas of bonding defining a plurality of pockets between the two layers of fibrous sheets in which the cosmetic component is trapped.

The fiber forming components of at least one, preferably both of the fibrous sheets may be water soluble or soluble in formulations that have water in them.

The fiber forming components of at least one, preferably both of the fibrous sheets, may have their glass transition temperature at, near or below a standard room operating temperatures such that they may be induced to flow under suitable pressures. Such temperatures may be in the range 1° C. to 35° C., or 5° C. to 30° C., or 10° C. to 30° C., or 15° C. to 30° C., or 15° C. to 25° C., or 16° C. to 25° C.

The polymeric material of the fibrous sheets may be selected from thermoplastic polymers, or polymer blends containing thermoplastic polymers with an amorphous component that can be deformed, and may include, but not be limited to, polyethylene oxide (PEO), polyethylene glycol (PEG), polyvinyl acetate (PVAc), polylactic acid (PLA), polycaprolactone (PCL), polyethylene terephthalate (PET), polypropylene (PP), polyvinyl chloride (PVC), polyvinylidene fluoride or polyvinylidene difluoride (PVDF), and Nylon.

The polymeric material of the fibrous sheets may in particular be selected from water soluble thermoplastic polymers, or polymer blends containing thermoplastic polymers with an amorphous component that can be deformed, and may include, but not be limited to, polyethylene oxide (PEO), polyvinyl pyrrolidone (PVP), polyethylene glycol (PEG), polyvinyl acetate (PVAc), polyvinyl alcohol (PVOH). These may be used in blends where desired and in combination with other water soluble polymers that do not serve as the primary agents for cold flow, including natural polymers such as Pullulan, Sodium Hyaluronate, Dextran, Starch or similar polysaccharides, Gelatin or Collagen or similar peptides, Sodium Alginate or synthetic water dispersible polymers such as water soluble polyacrylic/acrylate/acrylamide copolymers and their derivatives/copolymers.

Each fibrous sheet may have an average fiber diameter and fiber diameter distribution, and an area density suitable to entrap the dry cosmetic ingredient, based on the particle sizes, such that it does not noticeably fall through the structure.

Each fibrous sheet may dissolve in contact with a wet medium, with water as one of its constituents, to release the entrapped cosmetic ingredients.

At least one fibrous sheet may contain one or more additional cosmetic ingredient in the fibers that are released as the fibers dissolve in contact with a wet medium. Such additional cosmetic ingredients may include an antioxidant, emollient, humectant, active, surfactant or preservative. Such additional cosmetic ingredients may also be selected to provide adhesion to skin.

The additional cosmetic ingredient may be a humectant such as hyaluronic acid (HA), propylene glycol, sorbitol, butylene glycol, polyethylene glycol, sodium PCA, collagen, urea or glycerin, a moisturising ingredient such as an oil, for example squalane, jojoba oil, rosehip oil, sweet almond oil, olive oil, coconut oil, argan oil or other seed, vegetable or plant oils. The additional cosmetic ingredient may be a compatible surfactant or emulsifier such as sodium lauryl sulphate, cetrimonium chloride, cocamidopropyl betaine, alkyl polyglucosides, fatty acid esters of sorbitol such as polysorbate 80, or other suitable anionic, amphoteric, cationic or nonionic surfactants. The additional cosmetic ingredient may be an ingredient for addressing cosmetic concerns such as those reported to have anti-ageing, anti-inflammatory, anti-wrinkle, brightening, anti-acne or soothing properties. Non-exclusive examples include niacinamide, plant or fruit extracts, salicylic acid, glycolic acid, ubiquinone (CoQ10) and ceramides.

The dry cosmetic component may be selected from the cosmetic category of ingredients including but not limited to the following, and including any possible combination of mixtures thereof, beneficial active microbial species, beneficial inactive microbial species, microbial peptides, exfoliant/abrasive particles, cosmetically active ingredients, absorbent, cosmetic pigments, odour reducing ingredient, sun protection ingredient.

The dry cosmetic ingredient may be in a processable format including but not limited to powder, particle, flake, fiber or similar, and may be in a size range that does not result in large holes cut through the fibrous sheets when pressure is applied, and has a compression resistance range that allows it to yield under direct pressure.

The cosmetic component may be impregnated with cosmetic liquids, containing cosmetically active ingredients including a surfactant or emulsifier that will not dissolve or significantly distort or shrink the fibers.

An embodiment of the invention will now be described, by way of example only, with reference to the accompanying drawings.

BRIEF DESCRIPTION OF THE DRAWINGS

In the drawings:

FIG. 3 is a schematic representation of a method for preparing a cosmetic component;

FIG. 11 is a photograph showing the cosmetic component wetted out with oil in FIG. 8 with the substrate removed;

FIG. 12 is a photograph showing the cosmetic component in FIG. 11 with the substrate still attached;

FIG. 13 is a photograph of a cosmetic component showing hyaluronate powder distributed across a nanofiber layer;

DETAILED DESCRIPTION WITH REFERENCE TO THE DRAWINGS

There is provided a method for preparing a cosmetic component, such as a pad, patch, facial mask, including a full or split facial mask, roll, covering or the like, which has a laminated or layered construction. The method generally includes the steps of applying a layer of a dry cosmetic ingredient between a pair of fibrous sheets obtained by electrospinning polymeric material and subjecting the layers of fibrous sheets to sufficient pressure to the sheets to cause cold flow of at least some of the polymeric material such that at least parts of the sheets bond with each other and entrap the cosmetic ingredient in position between them.

Figure 1:
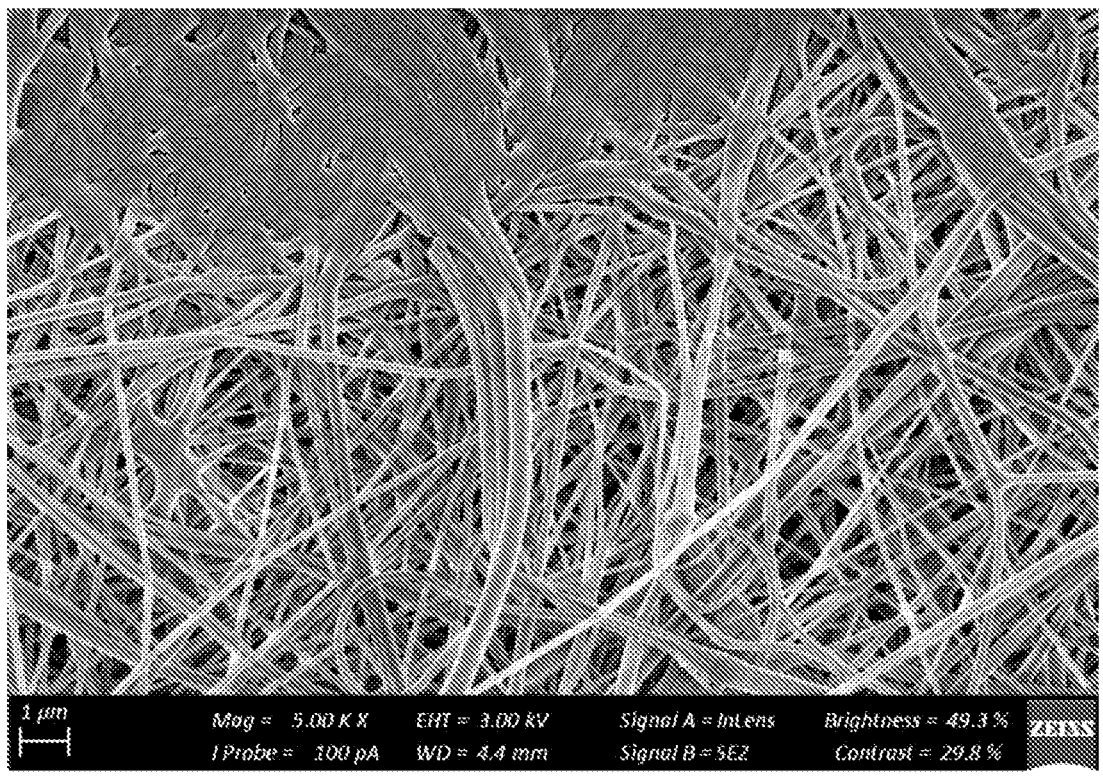
FIG. 1 is a SEM micrograph showing a nanofiber sheet, part of which has been cold pressed.
Figure 2A:
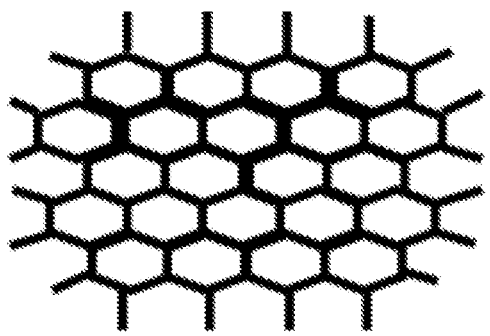
FIG. 2A to 2D illustrate exemplary bond patterns that can be applied during the preparation of a cosmetic component.
Figure 2B:
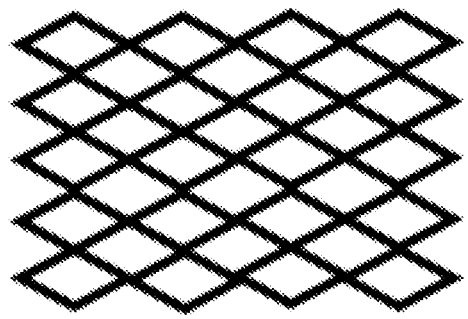
Figure 2C:
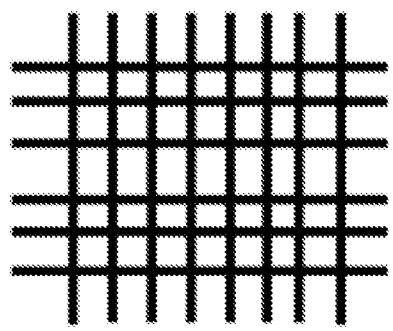
Figure 2D:
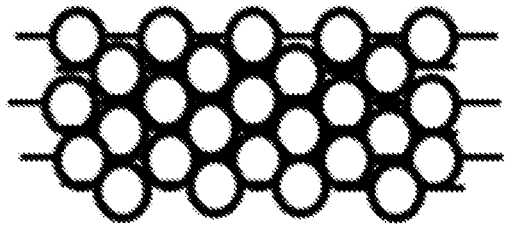

One or more polymeric materials may be used in the production of the fibrous sheets, but at least one should be capable of cold flow under pressure at low temperature, preferably room temperature. Cold flow is the tendency of glassy solid polymer material to deform permanently under the influence of sufficient stress as a function of time. Fundamentally, cold flow is the dramatic enhancement of polymer chain mobility and therefore lowers the glass transition temperature of glassy, or semi-crystalline, polymers if sufficient mechanical stress is applied. If sufficient stress is applied to two glassy polymer materials that are near their glass transition temperature at the testing or processing temperature (e.g. room temperature), no heat is required to make these polymers flow. These polymers can cold flow at the interface where they make contact, and will bond at the interface. If stress is applied to two glassy polymers but the polymers are well below their glass transition temperature, stress alone may not be enough to bond these materials at the interface. Nano-confinement at the surface of electrospun glassy polymers with submicron fiber diameters further would offer enhanced chain mobility at the interface between fiber segments, thereby further lowering the glass transition temperature, so that polymers well below their glass transition temperature can be induced to flow under sufficient stress. FIG. 1 shows a nanofiber material part of which has undergone cold flow (in the upper region of the image). "Cold" refers to operation temperatures at or below room temperature, as opposed to heat induced melting.

The conditions for cold flow are polymer dependent and based on a number of different variables including: composition, molecular weight, thickness, additives, format (nanofiber vs microfiber vs bulk film), time, yield strength, glass transition temperature, polymer morphology, thermal processing history, temperature, relative humidity (material conditioning) and force per unit area. Yield strengths of bulk polymers are typically in the Megapascal (MPa) range. Suitable pressures for inducing cold flow can be relatively easily determined by investigation for each fibrous sheet composition and will be apparent when trying to physically peel the nanofiber layers or sheets apart.

At least some of the fiber forming components of at least one, preferably both of the fibrous sheets, may have their glass transition temperature near or below standard room operating temperatures. Such room temperatures may be in the range 1° C. to 35° C., or 5° C. to 30° C., or 10° C. to 30° C., or 15° C. to 30° C., or 15° C. to 25° C., or 16° C. to 25° C. It will be appreciated, however, that even where the fiber forming components have their glass transition temperature above room temperature that they can still be induced to flow under suitable pressure. For example, PEO with average molecular weight of 200 k-300 k g/mol having a glass transition temperature of 67° C. will be induced to flow at room temperature under suitable pressure.

The polymeric material of the fibrous sheets may be selected from thermoplastic polymers, or polymer blends containing thermoplastic polymers with an amorphous component that can be deformed, and may include, but not be limited to, polyethylene oxide (PEO), polyethylene glycol (PEG), polyvinyl acetate (PVAc), polylactic acid (PLA), polycaprolactone (PCL), polyethylene terephthalate (PET), polypropylene (PP), polyvinyl chloride (PVC), polyvinylidene fluoride or polyvinylidene difluoride (PVDF), and Nylon.

The polymeric material of the fibrous sheets may in particular be selected from water soluble thermoplastic polymers, or polymer blends containing thermoplastic polymers with an amorphous component that can be deformed. These may include, but not be limited to, polyethylene oxide (PEO), polyvinyl pyrrolidone (PVP), polyethylene glycol (PEG), polyvinyl acetate (PVAc), polyvinyl alcohol (PVOH). These may be used in blends where desired and in combination with other water soluble polymers that do not serve as the primary agents for cold flow, for example natural polymers such as Pullulan, Sodium Hyaluronate, Dextran Starch or similar polysaccharides, Gelatin or Collagen or similar peptides, Sodium Alginate or synthetic water dispersible polymers such as water soluble polyacrylic/acrylate/acrylamide copolymers and their derivatives/copolymers.

Each sheet may have a different polymer or polymer mix and there is no requirement that the sheets have the same composition or structure.

Furthermore, the fibrous sheets can be in the form of electrospun webs or mats, or may have woven or knitted structure where fibers obtained from an electrospinning process, typically known as nanofibers, are formed into threads or yarns and then woven or knitted into sheets. The structure of these and the dry cosmetic ingredient should be selected to ensure that the dry cosmetic ingredient does not fall through the structure of the fibrous sheets.

Pressure is applied over the surface of the sheets using any suitable device. These are well known in the art and may include, for example, a roller press, stamp press plate, hydraulic press or the like. The "surface of the sheets (or cosmetic component)" is to be understood to mean the major opposed surfaces of the sheets or the exposed surfaces of the product formed by adjoining sheets. Pressure can furthermore be uniformly applied to the sheets so that cold flow is induced, and bonding occurs, over substantially the entire surface or area of the fibrous sheets. Pressure can alternatively be applied in a pattern, or along lines, extending over the surface of the fibrous sheets. Examples of such patterns are shown in FIGS. 2A to 2D. The patterned arrangement may include a plurality of intersecting lines and may be selected to form a plurality of pockets or enclosures in which the cosmetic ingredient is trapped. In this way substantial migration of the cosmetic ingredients during further processing or handling may be prevented and a substantially uniform distribution of the cosmetic ingredient maintained between the fibrous sheets. This may have significant benefits to the user as the cosmetic ingredient is prevented from collecting or clumping in a single corner of the cosmetic component such as occurs with the conventional "tea bag" construction. No special care needs thus be taken before use or during handling with the current cosmetic component to ensure a uniform application of the cosmetic ingredient to a skin surface or the like. It will be appreciated that such uniform application is highly desirable, especially where the cosmetic ingredient has a therapeutic or active cosmetic action. This overcomes difficulties in the prior art with some dry cosmetic ingredients will be altered negatively when exposed to moisture when including them in a liquid mix that may be required to provide a fixed concentration of an active ingredient. In such circumstances a dry product would then have to be provided in powdered form but the dosage cannot be easily controlled if metered out by the user from some powder dispenser and may not be easily spread to create a uniform treatment over the skin. In other cases, particular ingredients cannot be directly applied to the skin in uncontrolled concentration in this form as it would be dangerous, for example, higher concentrations of pH modifying ingredients such as salicylic or glycolic acid or ascorbic acid.

In order to prevent or reduce migration or movement of the cosmetic ingredient between the fibrous sheets it may be preferable, where a plurality of bond lines, or patterned bonding, is employed, to have a larger number of small pockets than a smaller number of large pockets.

Also, in order to prevent particles of the dry cosmetic ingredient from noticeably falling through the fibrous sheets, the average fiber diameter and fiber diameter distribution and area density may be selected to ensure an average pore size which is smaller than that of the particle sizes. It may not be possible to completely prevent particles falling through the structure of the fibrous sheets, especially during handling or manipulation of the cosmetic component, but any such migration through the sheets should not be significant or noticeable.

The dry cosmetic ingredients may be in a processable format including but not limited to powder, particle, flake, fiber or similar. Any suitable dry cosmetic ingredient may be used and may be of the cosmetic category of ingredients that includes, but is not limited to, the following, including any possible combination of mixtures thereof, beneficial active microbial species, beneficial inactive microbial species, microbial peptides, exfoliant/abrasive particles, cosmetically active ingredients, absorbent, cosmetic pigments, odour reducing ingredients and sun protection ingredients. The cosmetic components can be non-compatible in the wet-state but combined in the dry state. These can also be separated into different layers if needed.

Furthermore, the dry cosmetic ingredients may be selected to be in a size range that will not result in large holes cut through fiber sheets when pressure is applied. It may thus be possible for the particle sizes to be larger where the fiber sheets are thicker or more elastic than for thinner or less elastic fiber sheets. It may also have a compression resistance range that permits yielding under direct pressure.

The ambient temperature during the process may be maintained between 1° C. to 35° C., or 5° C. to 30° C., or 10° C. to 30° C., or 15° C. to 30° C., or 15° C. to 25° C., or 16° C. to 25° C., or room temperature. It is preferred that no heat be applied to the fibrous sheets during the process, in particular no heat through the device used to deliver pressure to the sheets.

A significant advantage of bonding the fibrous sheets together by inducing cold flow is that there is no need to remove dry cosmetic material from between the areas to be bonded. As no heat is applied to the fibrous sheets or to the dry cosmetic component, there is very little risk of heat induced changes to the physical or chemical properties of the dry cosmetic ingredient occurring. This significantly reduces the complexity of the process as any suitable methods can be used to apply the dry cosmetic ingredient between the layers and no special care need be taken to avoid specific areas, such as those intended to be bonded. A uniform distribution of the dry cosmetic ingredient can thus be obtained, if desired. It is also possible to bond or secure both sheets together across their entire adjoining surfaces if desired. This may be desirable where complete uniformity is required or desired.

The cosmetic component may be impregnated with cosmetic liquids containing cosmetically active ingredients. These may also include a surfactant or emulsifier if a cleansing function is required. Such impregnation may take place after bonding and any suitable method can be used to apply the cosmetic liquid to the cosmetic component. The cosmetic liquid should be selected such that it will not dissolve or significantly distort or shrink the fibers of the sheets. Where water soluble fibers are used, the cosmetic liquid should not contain water, or at least should not contain sufficient water to affect the fibers or the structure of the cosmetic component. For example, an oil based cosmetic cleanser may be applied. Such oil cleansers may consist predominantly of oils, oil soluble cosmetic ingredients and a combination of surfactants.

If desired, the cosmetic component may contain more than two layers of fibrous sheets and these may be secured together through pressure induced cold flow in any suitable order and in any suitable fashion. For example, all the layers can be bonded together simultaneously, or a first and second sheet could be bonded together and then a third bonded to the first and second. Moreover, in the latter example, the first and second layers could be bonded together using a different format or pattern to that used to bond the third layer to the bonded first and second sheets.

The cosmetic component need not be formed individually but could be cut or otherwise removed from a larger panel. Thus, large sheets of fibrous material with a cosmetic ingredient captured between them, as described above, may be manufactured and thereafter the individual cosmetic components removed from the resulting laminated structure. This may be done afterwards, for example by punching or cutting the cosmetic components out, or even during the pressure bonding stage, for example by incorporating a suitable cutting die into the device that applies pressure to the fibrous sheets.

Each fibrous sheet may dissolve in contact with a wet medium, with water as one of its constituents, to release the dry cosmetic ingredients.

At least one fibrous sheet may contain one or more additional cosmetic ingredient in the fibers that are released as the fibers dissolve in contact with a wet medium. Such additional cosmetic ingredients may include an antioxidant or preservative. The additional cosmetic ingredients may also be selected to provide adhesion to skin.

The additional cosmetic ingredient may be a humectant such as hyaluronic acid (HA), propylene glycol, sorbitol, butylene glycol, polyethylene glycol, sodium PCA, collagen, urea or glycerin, a moisturising ingredient such as an oil, for example squalane, jojoba oil, rosehip oil, sweet almond oil, olive oil, coconut oil, argan oil or other seed, vegetable or plant oils. The additional cosmetic ingredient may be a compatible surfactant or emulsifier such as sodium lauryl sulphate, cetrimonium chloride, cocamidopropyl betaine, alkyl polyglucosides, fatty acid esters of sorbitol such as polysorbate 80, or other suitable anionic, amphoteric, cationic or nonionic surfactants. The additional cosmetic ingredient may be an ingredient for addressing cosmetic concerns such as those reported to have anti-ageing, anti-inflammatory, anti-wrinkle, brightening, anti-acne or soothing properties. Non-exclusive examples include niacinamide, plant or fruit extracts, salicylic acid, glycolic acid, ubiquinone (CoQ10) and ceramides.

The method may include laying down a first fibrous sheet, applying the dry cosmetic ingredient to the uppermost surface of the first fibrous sheet, laying a second fibrous sheet over the dry cosmetic ingredient, and subjecting the layers of fibrous sheets to sufficient pressure to cause at least parts of the nanofiber sheets to bond with each other and entrap the cosmetic ingredient in position between them.

The cosmetic component may subsequently be removed from the laminated sheets by cutting, punching or the like. The cosmetic component may also be removed from the sheets by a cutting die while pressure is being applied to them. The cosmetic component may be further processed or packaged.

A schematic illustration of a method of preparing a cosmetic component is provided in FIG. 3. In this embodiment a first or lowermost fibrous sheet (10) is laid on a generally flat surface (not shown). The fibrous sheet (10) is made through an electrospinning process from one or more polymeric materials at least one of which is capable of cold flow under pressure. A dry cosmetic ingredient (12) is then evenly sprinkled over the entire upper surface (14) of the first sheet (10). Hereafter a second or uppermost fibrous sheet (20) is laid on top of the first sheet (10) with the dry cosmetic component (12) therebetween to form a layered or sandwich structure (22). The first sheet (10) and second sheet (20) will preferably have complementary shapes to minimise waste.

The second fibrous sheet (20) has the same composition as the first sheet (10), but this need not be the case and the second sheet (20) could have a different composition to the first sheet (10).

The layered structure (22) is then subjected to pressure, in this embodiment by feeding it end first through a roller press (24). In this embodiment too, the rolls (26, 28) of the press are both smooth and thus apply substantially uniform pressure across the width of the fibrous sheets (10, 20) as they pass between the rolls (26, 28). The pressure applied by the roller press (24) is sufficient to cause cold flow of some of the polymeric material. This in turn results in the first sheet (10) and the second sheet (20) becoming bonded together across their width with the dry cosmetic ingredient trapped between them. Once the entire layered structure (22) has passed through the roller press (22), its entire surface area will have been subjected to pressure and the fibrous sheets (10, 20) will be laminated or bonded together over their entire adjoining surfaces. It will be understood that the polymeric cold flow may occur about the particles of the dry cosmetic ingredient and that the sheets (10, 20) may not be directly bonded together at the area occupied by a particle.

Either or both fibrous sheets could be carried on a backing or support sheet or substrate on their non-abutting or adjoining sides and this could be removed during or after processing. Where a mesh-like supporting sheet is used, and maintained on the fibrous sheets during pressing with smooth rollers, a bonding pattern will be created by the mesh. In other words, cold flow, and hence bonding, will take place along areas corresponding to the mesh.

The ambient temperature is maintained at room temperature, in this case between 18° C. and 20° C., and the rolls (26, 28) are not heated.

The product from the roller press (24) is a large, flexible panel (30). A plurality of cosmetic components (32), in this embodiment rectangular patches, are subsequently removed from the panel (30) by inserting the panel in a cutting die (not shown) operated by a press (36). The cutting die has blades (not shown) which are configured to simultaneously cut multiple patches from the panel (30). Once cutting has been performed the resultant patches (32) are removed from the press (36) and then individually packaged in sealed, high barrier laminated foil packaging (not shown).

Figure 4:
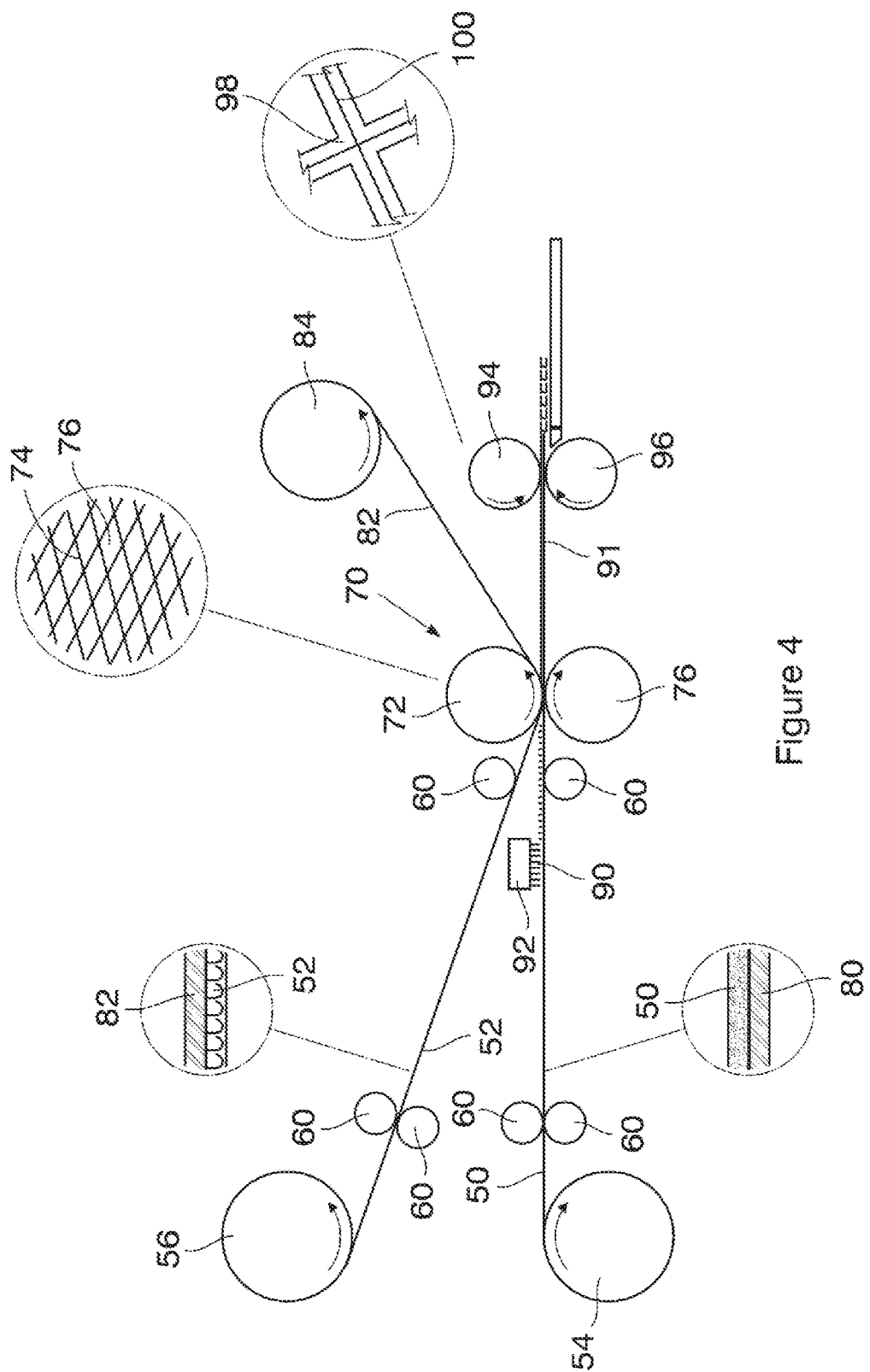
FIG. 4 is a schematic representation of a further method for preparing a cosmetic component.

A schematic illustration of a further method of preparing a cosmetic component is provided in FIG. 4. While the previous embodiment illustrated a batch process, this embodiment illustrates a continuous process for making a cosmetic component. As illustrated, two fibrous sheets (50, 52) or webs are drawn from horizontally spaced apart rolls (54, 56), using suitable guide rollers (60), through a roller press (70). Each sheet (50, 52) is carried on a polymeric mesh substrate (80, 82). The lowermost sheet (50) is carried on top of the substrate (80) and the uppermost sheet (52) is carried below the substrate (82).

Before entering the roller press (70), a dry cosmetic ingredient (90) is deposited (92), for example by sprinkling, spraying or other suitable means, onto the lowermost sheet (50) across its width. The pressure applied by the roller press (70) is selected or adjusted to obtain cold flow of the polymeric material, or at least part thereof, of the fibrous sheets (50, 52) to cause them to bond together about the dry ingredient (90).

In this embodiment, one roller (72) has a raised diamond mesh pattern (74), as illustrated in the inset, on its surface through which pressure is applied to the fibrous sheets and dry cosmetic ingredient. This results in cold flow, and hence bonding or lamination, only along areas which correspond to the raised surface. A diamond mesh pattern of cold flow bonds thus secures the two sheets (50, 52) together with small, diamond shaped pockets (76) of unbonded material between, and defined by, the bonded areas. The dry cosmetic ingredient (90) is trapped between the sheets (50, 52) in the bonded areas and also in the pockets (76).

After exiting the roller press (70) the substrate (82) of the uppermost sheet (52) is removed and wound onto a drum (84).

The bonded or laminated structure (91) is then fed between a further set of rollers (94, 96) the purpose of which is two-fold, to create a bonded border defining individual components, and to remove the components from the laminated structure (91). To this end a raised rectangular pattern (98) is provided on one roller (94) with a blade (100) extending centrally along each raised line or ridge. Slots or grooves (not shown) complementary to the blades (100) are provided in the opposite, otherwise smooth roller (96). The rollers may be indexed to ensure correct alignment of the blades and slots in use. As the laminated structure (91) passes through the rollers (94, 96), the ridges (98) apply sufficient pressure to cause a further cold flow bond in the laminated structure while the blades (100) cut the individual cosmetic components from the structure. These may then be further processed or packaged.

To provide an even more continuous process, instead of rolls (54, 56) of fibrous material being used, electrospun webs, which may be carried on substrates, could be drawn directly from suitable electrospinning apparatuses, for example, the apparatus shown in WO 2008/062264.

Numerous modifications or improvements to the above illustrated processes will be apparent to one skilled in the art.

The cosmetic component which results from the process includes two layers of fibrous sheets, obtained by electrospinning one or more polymeric materials, which are secured together in at least one area of bonding created through cold flow of at least some of the polymeric material. A dry cosmetic component is provided between the layers and may extend into each area of bonding. Thus, there is no need to take special precautions to ensure that the dry cosmetic component does not extend into the bonded areas, as required by prior art processes.

The polymeric material of the fibrous sheets may be selected from water soluble thermoplastic polymers, or polymer blends containing thermoplastic polymers with an amorphous component that can be deformed, and may include, but not be limited to, polyethylene oxide (PEO), polyvinyl pyrrolidone (PVP), polyethylene glycol (PEG), polyvinyl acetate (PVAc), polyvinyl alcohol (PVOH) and various co-polymers thereof. These may be used in blends where desired and in combination with other water soluble polymers that do not serve as the primary agents for cold flow e.g. natural polymers such as Pullulan, Sodium Hyaluronate, Dextran or similar sugars, Gelatin or Collagen or similar peptides, Starch or other polysaccharides, Sodium Alginate or synthetic water dispersible polymers such as water soluble polyacrylic/acrylate/acrylamide copolymers and their derivatives/copolymers.

The requirements for the dry cosmetic ingredient are merely that it be in a suitable form for processing and that it not result in excessive damage to the structure of the cosmetic component during processing. Thus, where it is provided in a granular or particulate form, its particle size range should not result in large holes being cut through the fibrous sheets when pressure is applied to these. Also, the compression resistance range of the particles should allow yielding under direct pressure. As the current process is performed at or close to room temperature, there is no requirement for the dry cosmetic ingredient to be stable at high temperatures. The dry cosmetic component may be in any suitable form, including powder, particle, flake, and fiber.

The dry cosmetic component may be selected from the cosmetic category of ingredients. These may include beneficial active microbial species, beneficial inactive microbial species, microbial peptides, exfoliant/abrasive particles, cosmetically active ingredients, absorbent, cosmetic pigments, odour reducing ingredients and sun protection ingredients. Mixtures of these or any other suitable ingredients may be used.

If desired, the cosmetic component may be impregnated with cosmetic liquids containing cosmetically active ingredients including a surfactant or emulsifier. These should be selected such that they will not dissolve or significantly distort or shrink the fibers of the sheets. For example, an oil based cosmetic cleanser may be applied. Such oil cleansers may consist predominantly of oils, oil soluble cosmetic ingredients and a combination of surfactants.

The fibrous sheets of the cosmetic component are bonded in such a way that migration or movement of the dry cosmetic ingredient is limited or eliminated. The bonding area can thus extend over the entire surface of the cosmetic component, or substantial part of it. Alternatively, small pockets or enclosures can be created between the sheets using lines of bonding, preferably intersecting lines of bonding, which extend over the surface of the cosmetic component. Such lines or areas of bonding may take a patterned format for both aesthetic appeal and practical repeatability.

In order to prevent the dry cosmetic ingredient from escaping through the structure of the sheets, these may have fibers with an average fiber diameter and fiber diameter distribution, and an area density, suitable to entrap the dry cosmetic ingredient. These parameters may be based on the particle sizes of the dry cosmetic ingredient and selected such that particles do not noticeably fall through the structure and are substantially retained between the fibrous sheets.

The fiber forming components of at least one, preferably both of the fibrous sheets may be water soluble or soluble in formulations that have water in them. Such formulations may include water based facial cleansers or moisturisers and the like. It may be desirable that each fibrous sheet dissolve in contact with a wet medium, with water as one of its constituents, to release the dry cosmetic ingredients.

Different polymers or blends may be used to prepare the sheets. These could be either or both hydrophilic or hydrophobic. However, the polymers should generally be of the class of water soluble polymers as to allow the cosmetic ingredients to be instantly released to the skin when activated by a water or a typical cosmetic liquid or spray or mist containing water.

At least one fibrous sheet may contain one or more additional cosmetic ingredient in the fibers that are released as the fibers dissolve in contact with a wet medium. Such additional cosmetic ingredients may include an antioxidant or preservative. Such additional cosmetic ingredients may also be selected to provide adhesion to skin.

An example of an additional cosmetic ingredient is hyaluronic acid (HA). The HA may be incorporated into the fibers during the electrospinning process.

Either or both of these layers could also encapsulate other active ingredients within the nanofibers.

The cosmetic component may have more than two layers and these may be secured together in any suitable order or arrangement. The cosmetic component may include multiple sheets or layers with multiple entrapped solids, and the entrapped solids do not have to be of the same type. For example, a mild exfoliant and salicylic acid either mixed together between two layers or separated with a third layer in between them could be used.

Layers of different planar density, or other characteristics, can be used provided that there is a thermoplastic component which permits cold flow to be achieved.

As indicated above, the sheets may have any suitable structure of fibrous material. They may be obtained by electrospinning fibers onto a collector to form a web, pad or mat-like structure. Alternatively, electrospun fibers may be formed into threads or yarns and these used to create the sheets by knitting or weaving the threads or yarns. The sheets may also each have a different structure.

Sheets of nanofiber material are often supported on a substrate or sheet or backing layer to assist in maintaining their structural integrity and improve handling or processing ability. Such substrates may be films (solid or porous) or textiles (knitted, woven or non-woven or a combination thereof). They may be made of metals such as aluminium foil or from natural or synthetic polymers or some combination thereof. Where appropriate, these substrates may be removed prior to processing or retained during processing and removed thereafter, such as prior to packaging or prior to use. Also, where a mesh substrate is used, the substrate-nanofiber surface area percentage may be increased or decreased based on the substrate mesh count and wire diameter and nanofiber thickness.

The cosmetic component produced by the method disclosed may allow for the delivery of homogeneously distributed dry cosmetic active ingredients pressed between layers of nanofibers with or without a support. This allows for a greater degree of control over dosage per surface area of active ingredients and may permit the use of a wide range of cosmetically relevant additives of compatible and incompatible nature without incurring a loss of material quality or production time.

Standard welding (melt or solvent) requires melting or dissolving (so the formation of two liquids) of surfaces to create a mixing of molecules and setting (bonding or fusion) of the two surfaces together. Cold flow welding is different in that there is only a liquid-like flow of amorphous regions of the polymers and the polymers do not behave as true liquids, in that their kinetic energy is lower and they do not flow to the same degree as true liquids.

The bond strength is also very different. Typically, a far superior bond strength is obtained with molten or solvent welding than with cold welding. In cold flow welding there is superficial bonding with the surface layers between two interfaces, but with solvent or molten welding there is bonding in deeper layers and typically through a thin fiber structure such as used in the present cosmetic component.

Importantly, the heat or solvent used in heat or solvent welding may degrade, denature or distort dry cosmetic ingredients and also distort the cosmetic component. In the case of solvent welding the solvent may dissolve the fibers or the dry cosmetic ingredients.

The effect of solvent or heat is far more significant with nanofibers, as compared to a "bulk" material or thicker film, as the material is so thin and the nanofibers are typically in a semi-strained state as the fibers are stretched and the aligned polymer chains frozen in place when the solvent leaves and dry nanofibers are collected during electrospinning. A small amount of heat or solvent can have consequently a significant effect.

The pressure selected to form the cosmetic component in the present method is sufficient to bond the fibrous layers, to deliver the cosmetic ingredient in a suitable format for the application and to not destroy the fibers by any significant degree.

Bonding two nanofiber sheets together using pressure only at room temperature removes the need for commonly used methods in the prior art that would damage or distort or add some additional chemicals to the fine nanofiber sheets, for example methods using heat, chemical or needle felting.

Due to the damaging methods of bonding used in the prior art, only "tea-bag" type structures are taught in which pads of nanofibers are joined together by creating a seal on the periphery or circumference of the component. The present method permits a complete or patterned bond across the entirety of the two bonded nanofiber sheets that is bonding two nanofiber sheets across the x-y plane. This not only assists in ensuring a uniform distribution of the dry cosmetic ingredient by preventing its migration or movement between the sheets, but also may assist in providing greater mechanical strength to the cosmetic component. Nanofibers are typically bonded to a substrate to compensate for their fragility and lack of mechanical strength for intended applications but bonding them together across the entirety of their surfaces may provide the resultant product with sufficient strength or integrity to avoid the use of a substrate or backing as support.

Example 1

An example of a cosmetic component was prepared as follows. An aqueous blended polymer solution containing Pullulan (average molecular weight 200 kDa), polyethylene oxide (average molecular weight 250 kDa), polysorbate 80, and Sodium Hyaluronate (average molecular weight between 10-35 kDa, and most preferably between 10-15 kDa) was prepared in the ratio of 73.3/13.3/8.3/5 wt % (based on the dry polymer loading), where the concentration in solution was 13.6/2.5/1.5/0.9 wt % respectively.

Proprietary SNC BEST™ technology was used to electrospin the fibers, from the resulting solution blend, to a planar density range within 1.7-3.2 gsm and an average fiber diameter range of 200-250 nm onto a substrate layer of polyester hexagonal netting to produce a first sheet or layer (200), measuring approximately 1 m×5 m, on substrate (205), where the substrate layer has a planar density of 38 gsm and a wire diameter of 185 μm, but any suitable substrate layer may be used.

Figure 6:
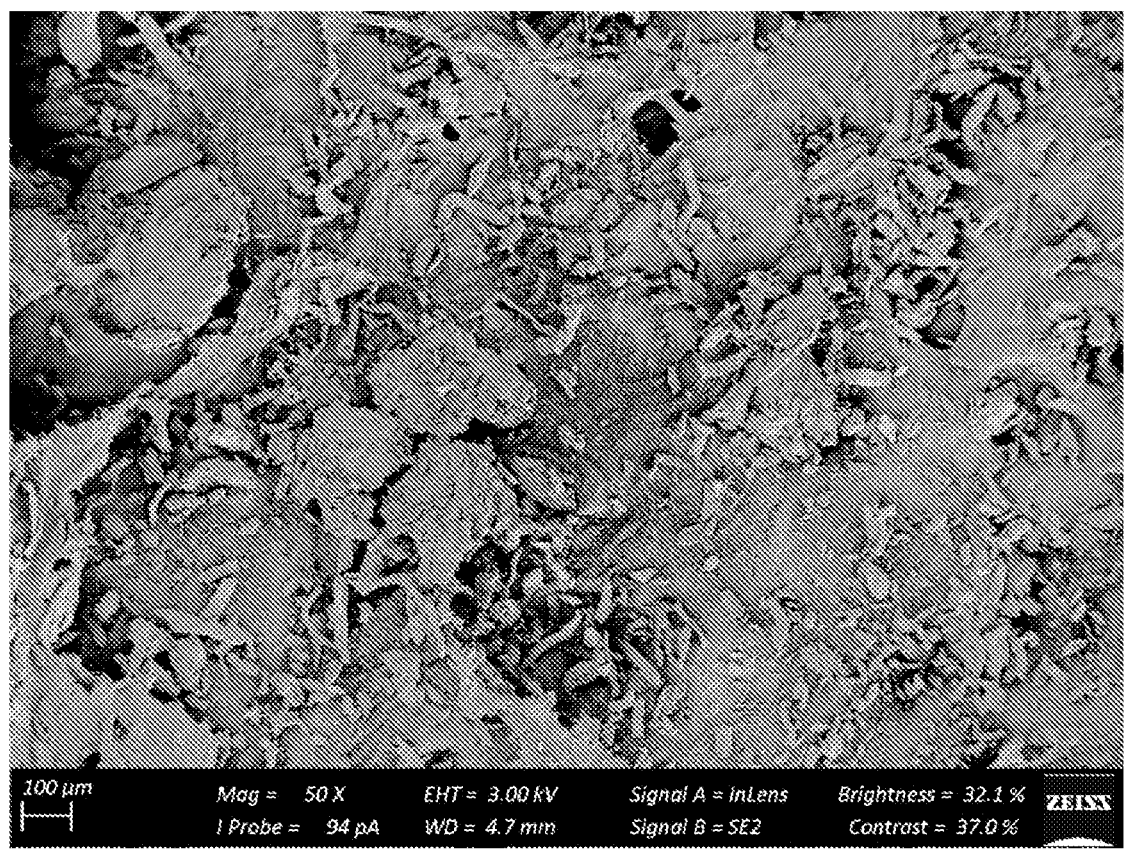
FIG. 6 is a SEM micrograph showing an example of a cosmetic component showing microcrystalline cellulose distributed across a nanofiber layer.
Figure 7:
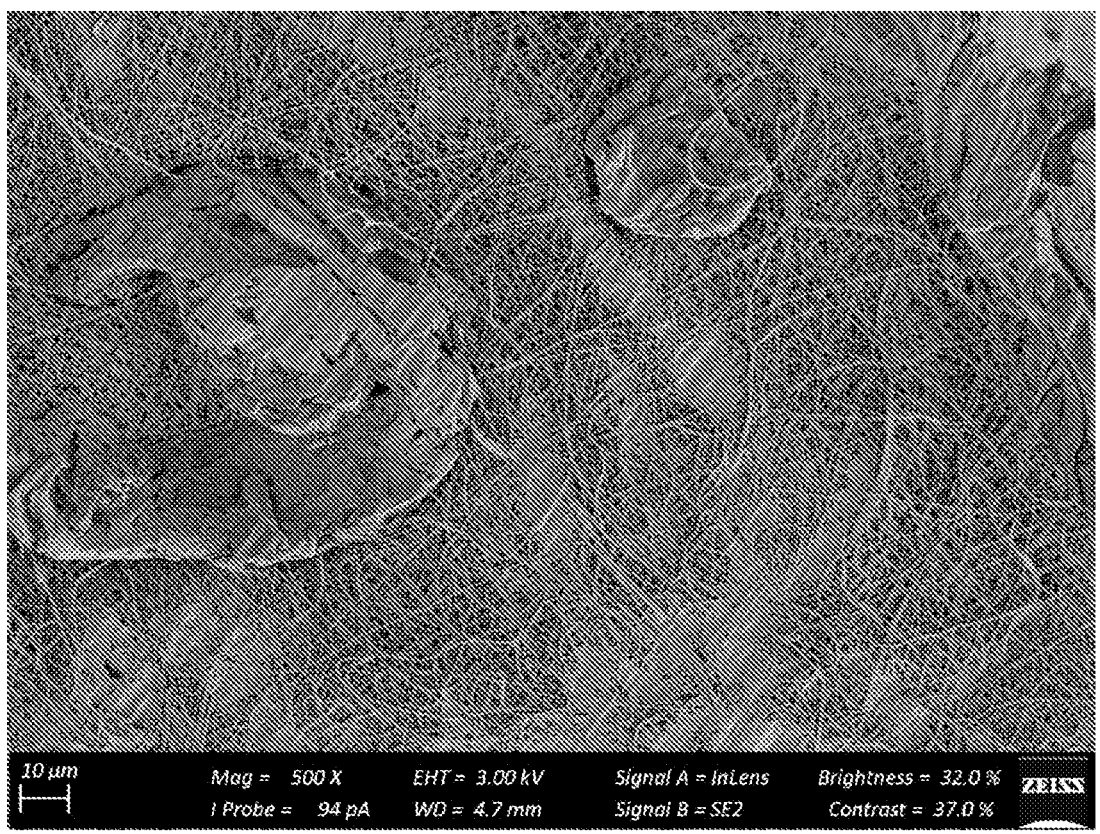
FIG. 7 is a SEM micrograph of the cosmetic component in FIG. 6 showing space between microcrystalline cellulose particles distributed across a nanofiber layer and lines of bonding where cold flow has occurred.

Microcrystalline cellulose exfoliant was then dispersed uniformly onto the surface of the first sheet or layer (200), nanofiber side up, until a dosage between 3-4 mg/cm$^2$, and most preferably between 3.3-3.5 mg/cm$^2$, was achieved to form a layer (210). FIG. 6 shows distribution of the microcrystalline cellulose over the entire surface of the sheet (200). From FIG. 7 it can be seen that space exists about individual particles to permit cold flow to occur.

A second nanofiber sheet or layer (220) of the same material and properties as the first (200), and also spun onto a substrate (225) is then placed nanofiber side down on top of the exfoliant layer (210).

Figure 5:
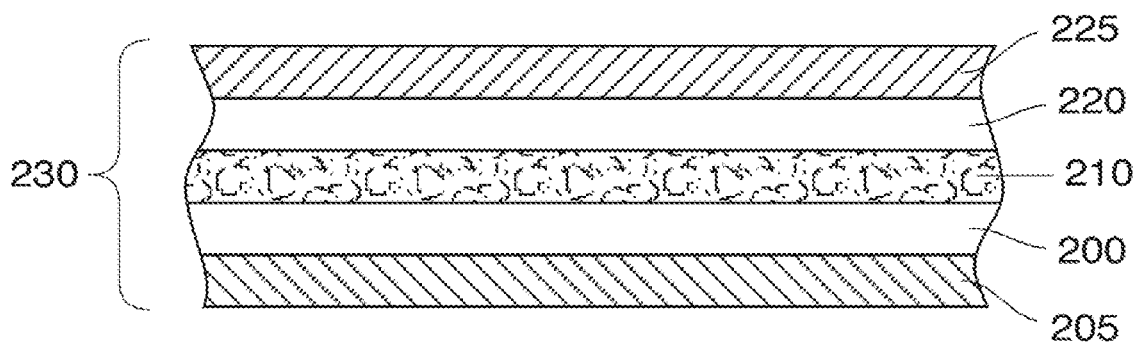
FIG. 5 is a cross-sectional illustration of an example embodiment of a cosmetic component in accordance with the present invention.

The resulting stacked layers, providing a layered or sandwich structure (230), as shown in FIG. 5, was then consolidated by pressing the entirety of the structure (230). To achieve this a 1.5 mm stainless steel 316/304 shim was placed on top of the layered structure which was then passed through a Keip Bros etching press at setting 2.5-3.5 at ambient environmental conditions. This setting was determined experimentally.

Figure 8:
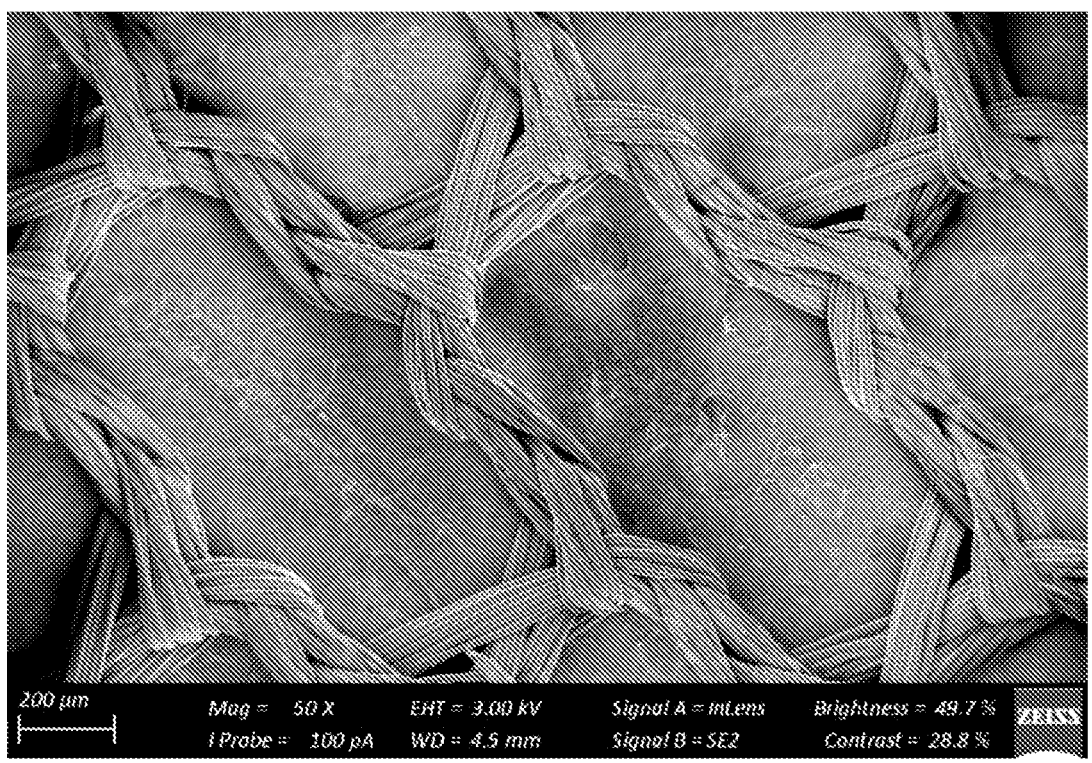
FIG. 8 is a SEM micrograph showing an example of a cosmetic component after cold pressing with a substrate in place.

A large bonded panel results with a nanofiber-nanofiber bonding surface area of ca. 100% and a substrate-nanofiber bonding surface area of 14-34%. FIG. 8 is a SEM micrograph of part of one side of the product after cold pressing with a substrate in place on a nanofiber sheet.

Figure 9:
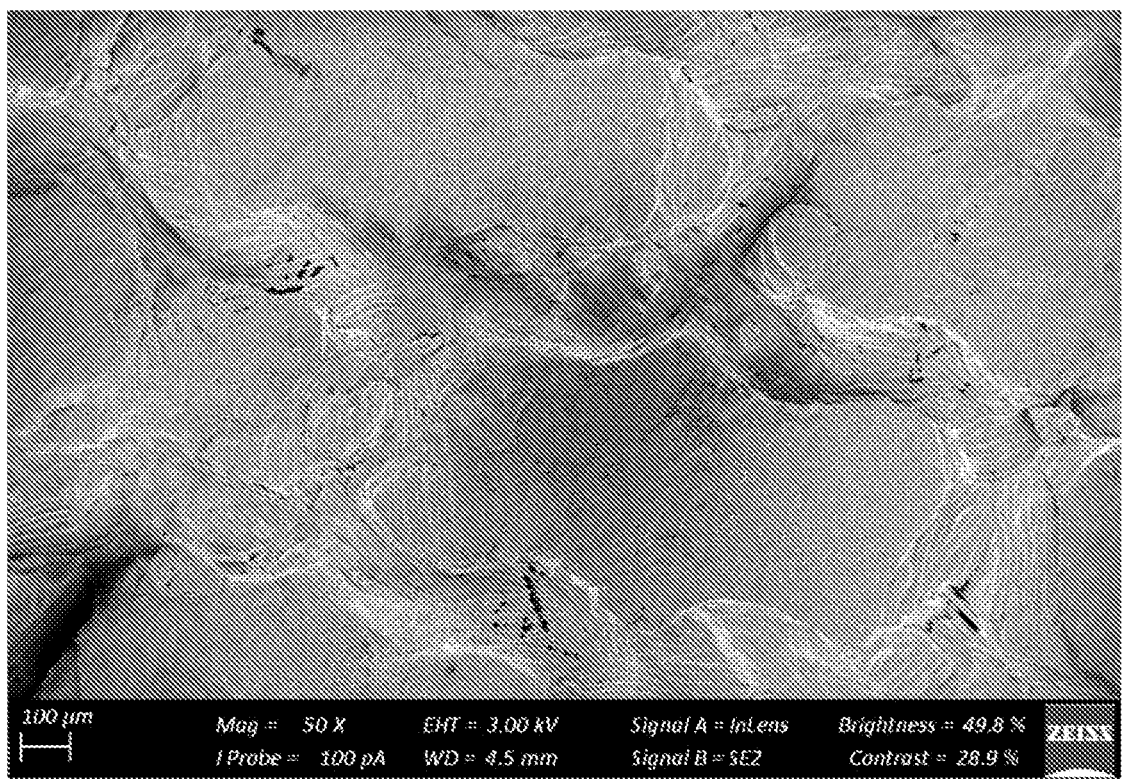
FIG. 9 is a SEM micrograph showing the cosmetic component in FIG. 8 with the substrate removed and the occurrence of cold flow.
Figure 10:
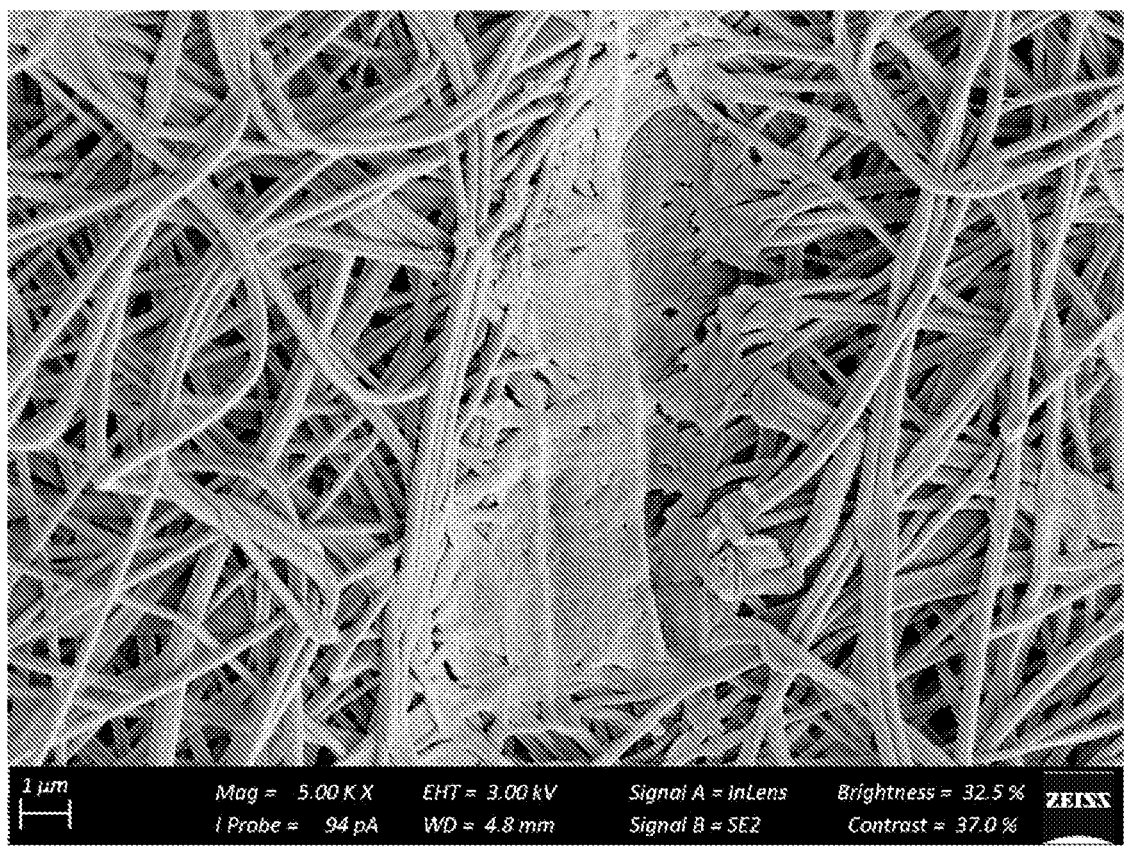
FIG. 10 is a SEM micrograph showing the cosmetic component in FIG. 8 with the substrate removed and illustrating cold flow in nanofibers abutting the substrate.

At this point one, or both, of the substrate layers (205, 225) may be removed from the nanofiber sheets (200, 220). In this example the substrate layer was removed from only one side. FIG. 9 is a SEM micrograph of part of one side of the product after cold pressing with the substrate removed from the nanofiber sheet. FIG. 10 is a SEM micrograph showing part of the cosmetic component with the substrate removed and illustrates cold flow in nanofibers abutting or adjoining the substrate. As pressure is applied or transmitted through the mesh substrate the nanofibers abutting the mesh undergo irreversible cold fusion.

After pressing the nanofiber layers were no longer able to be separated without damaging them.

The panel was then further processed as follows:

Individual oval components of 7.5×5.0 cm were cut from the panel with a cutting die having a plurality of stainless steel oval blades and used on a Tippmann motorized roller cutter shimmed with a cutting board of 2 mm thickness. After cutting, the individual cosmetic components were gently removed from the die. FIG. 11 illustrates one side of an oval cosmetic component with the substrate layer removed and FIG. 12 illustrates the opposite side with the substrate layer attached.

The individual ovals were then impregnated with 0.015-0.020 mL/cm$^2$ of custom formulation oil cleanser. In this example the oil cleanser was applied using a self-refilling automatic syringe. The oil is of a suitable viscosity (not measured) that it can wet out and impregnate the entirety of the ovals within several minutes.

The ovals were then stacked 3 ovals high interlaced with PET film separator layers. The 3 oval stack is then placed in a V-folded PET film sheet and sealed in a high barrier foil sachet.

The directions for use of the cosmetic components are as follows:

Carefully remove the V-folded PET film enclosing the patch from the package. With dry hands, remove a patch from the film. Apply the patch to the desired part of the face and peel off the white mesh. Allow the oil cleanser to settle for 1-2 minutes. Wet your face by patting gently with wet hands, or use a fine water mist or spray to evenly wet out the whole patch. Rub in small circular motions for 1 minute to exfoliate, avoiding the eye area. Rinse well to remove residue.

Example 2

An example of a cosmetic component was prepared as follows. An aqueous blended polymer solution containing Pullulan (average molecular weight 200 kDa), polyethylene oxide (average molecular weight 250 kDa), polysorbate 80, and Sodium Hyaluronate (average molecular weight between 10-35 kDa, and most preferably between 10-15 kDa) was prepared in the ratio of 73.3/13.3/8.3/5 wt % (based on the dry polymer loading), where the concentration in solution was 13.6/2.5/1.5/0.9 wt % respectively.

Proprietary SNC BEST™ technology was used to electrospin the fibers, from the resulting solution blend, to a planar density range within 1.7-3.2 gsm and an average fiber diameter range of 200-250 nm onto a substrate layer of polyester hexagonal netting to produce a first sheet or layer, measuring approximately 1 m×5 m, on substrate, where the substrate layer has a planar density of 38 gsm and a wire diameter of 185 µm.

Figure 14:
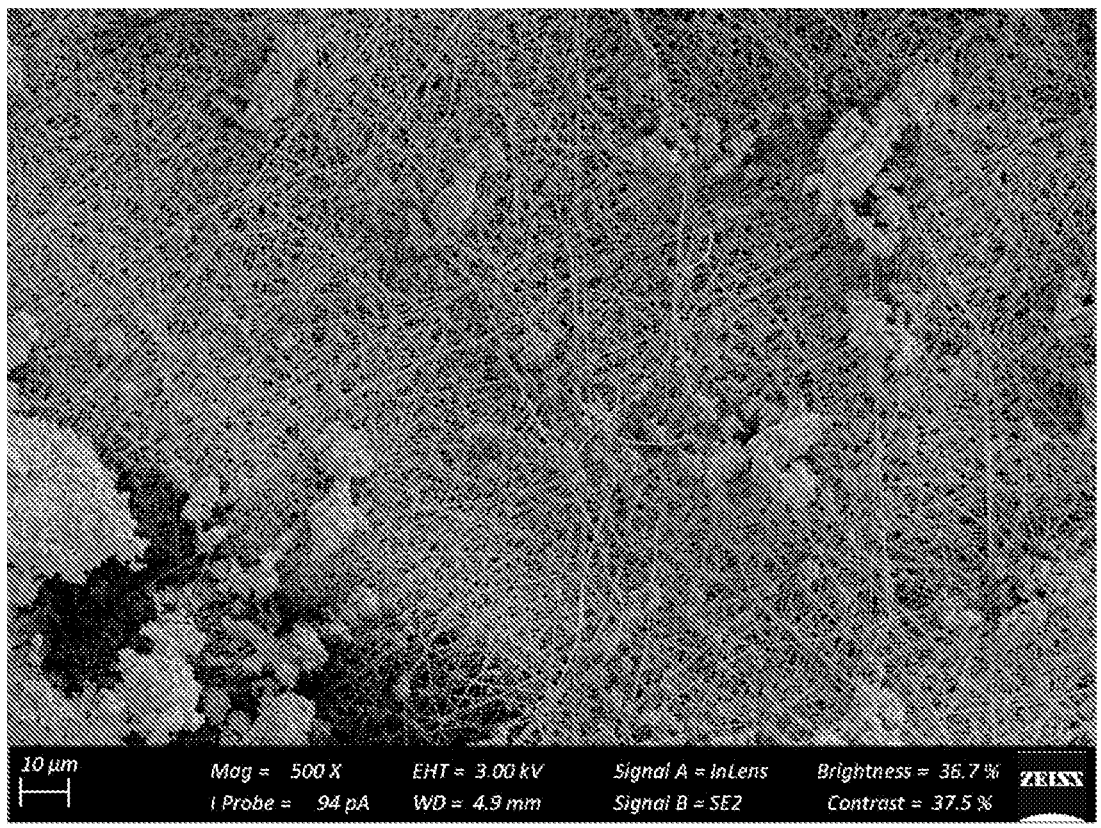
FIG. 14 is a SEM micrograph of the cosmetic component in FIG. 13 showing the hyaluronate powder distributed across the nanofiber material.
Figure 15:
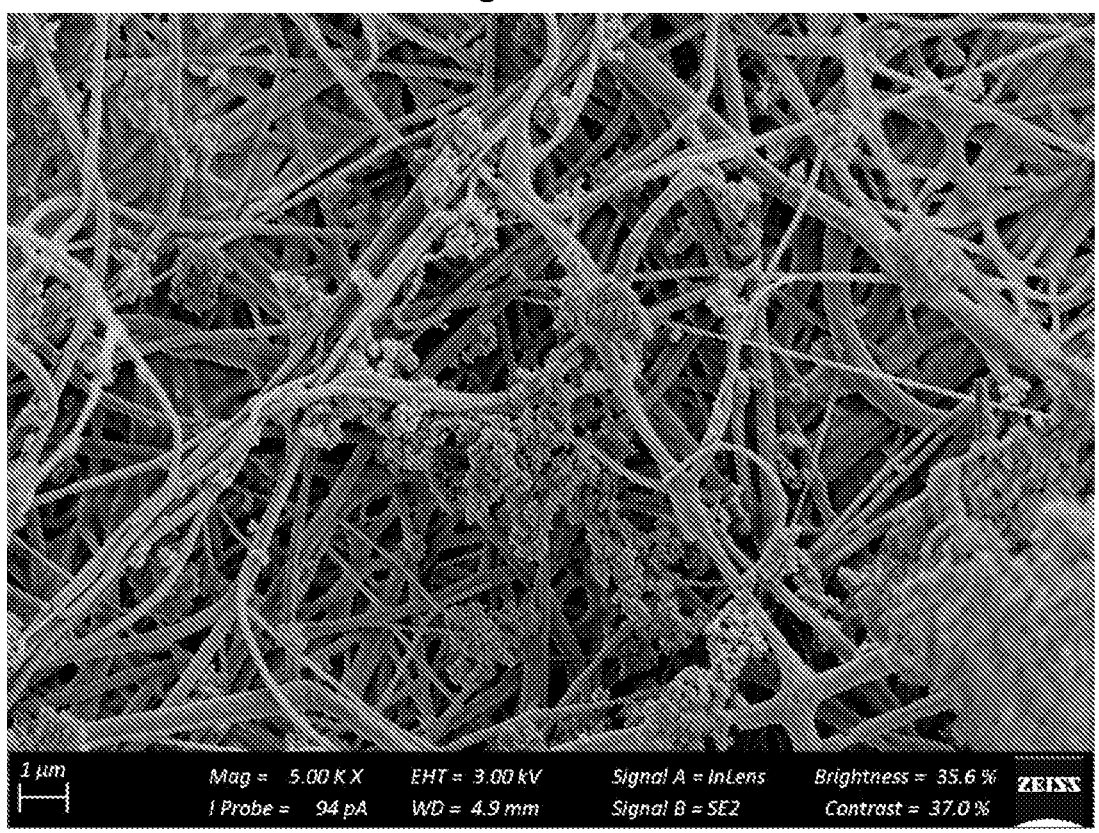
FIG. 15 is a higher magnification SEM micrograph of the cosmetic component in FIG. 13 showing the hyaluronate powder distributed across the nanofiber material.

Sodium Hyaluronate (average molecular weight between 10-35 kDa, and most preferably between 10-15 kDa) was then dispersed uniformly onto the surface of the first sheet or layer, nanofiber side up, until a dosage between 3-4 mg/cm$^2$, and most preferably between 3.3-3.5 mg/cm$^2$, was achieved to form a layer, as shown in FIG. 13. FIGS. 14 and 15 are SEM micrographs showing the hyaluronate powder distributed across the nanofiber sheet.

A second nanofiber sheet or layer of the same material and properties as the first, and also spun onto a substrate is then placed nanofiber side down on top of the Hyaluronate layer.

The resulting stacked layers, providing a layered or sandwich structure, was then consolidated by pressing the entirety of the structure. To achieve this a 1.5 mm stainless steel 316/304 shim was placed on top of the layered structure which was then passed through a Keip Bros etching press at setting 2.5-3.5 at ambient environmental conditions. This setting was determined experimentally.

Figure 16:
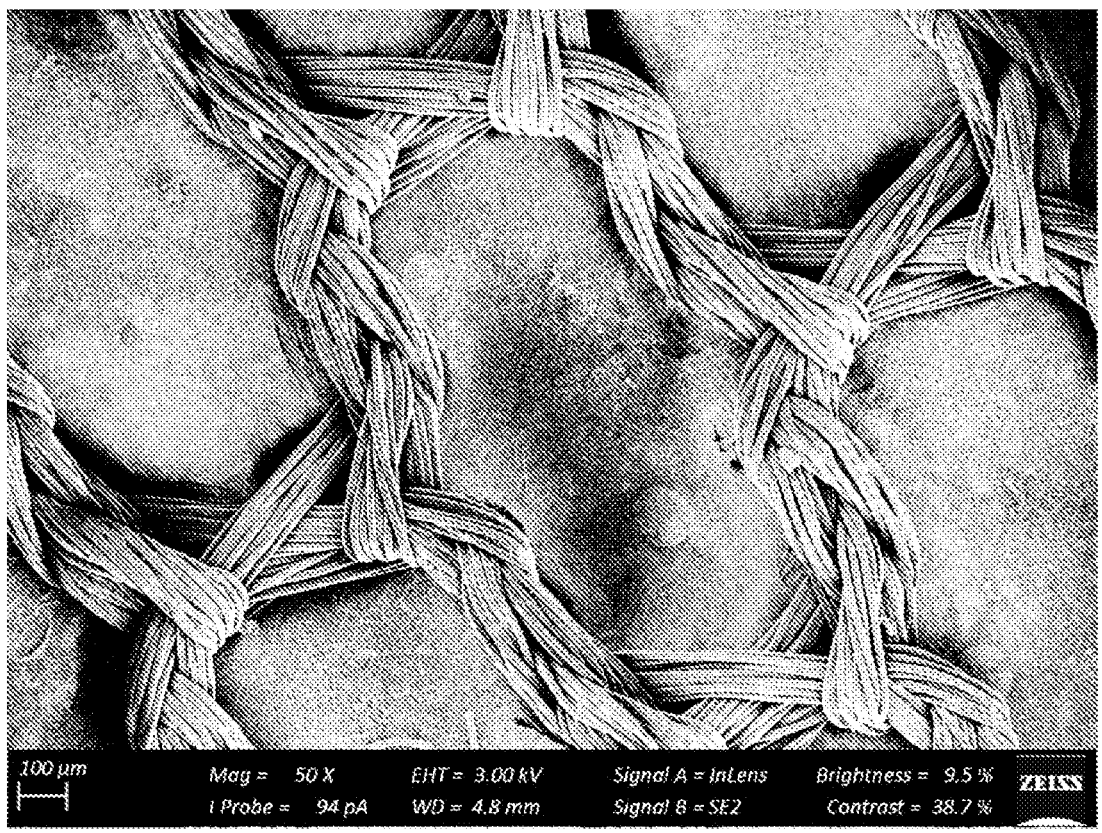
FIG. 16 is a SEM micrograph of the cosmetic component in FIG. 13 showing the mesh substrate to have made an indentation on the nanofiber layer after pressing.

A large bonded panel results with a nanofiber-nanofiber bonding surface area of ca. 100% and a substrate-nanofiber bonding surface area of 14-34%. FIG. 16 is a SEM micrograph of part of one side of the product after cold pressing with the substrate in place on the nanofiber sheet.

Figure 17:
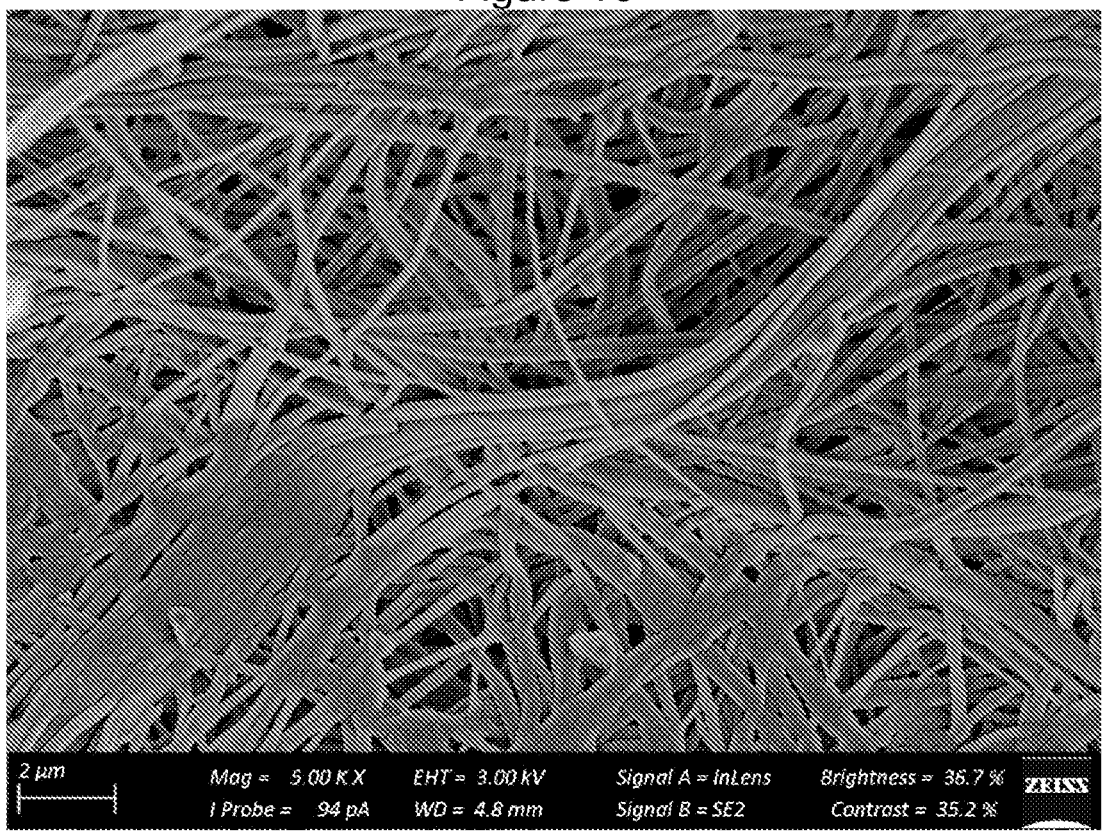
FIG. 17 is a SEM micrograph of the cosmetic component in FIG. 16 showing cold flow of the nanofiber material abutting the mesh substrate.
Figure 18:
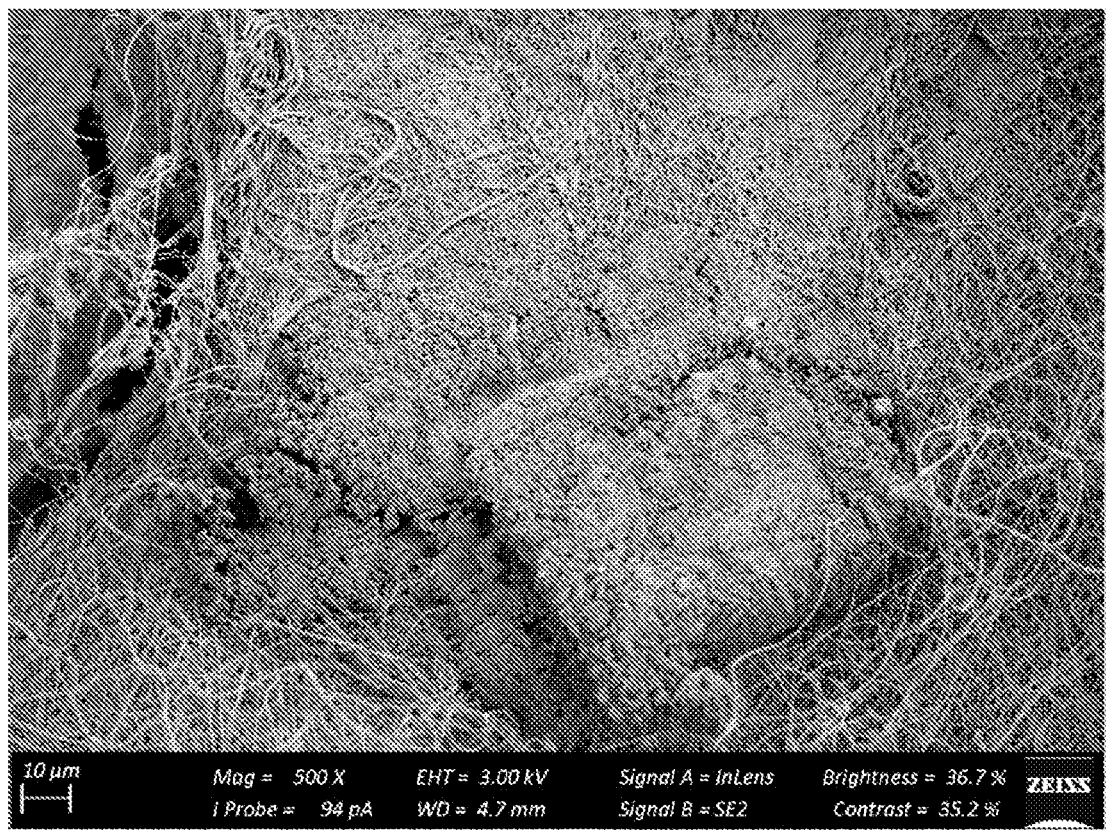
FIG. 18 is a SEM micrograph of the cosmetic component in FIG. 13 after pressing showing hyaluronate powder in a region of cold flow in the nanofiber material layer.
Figure 19:
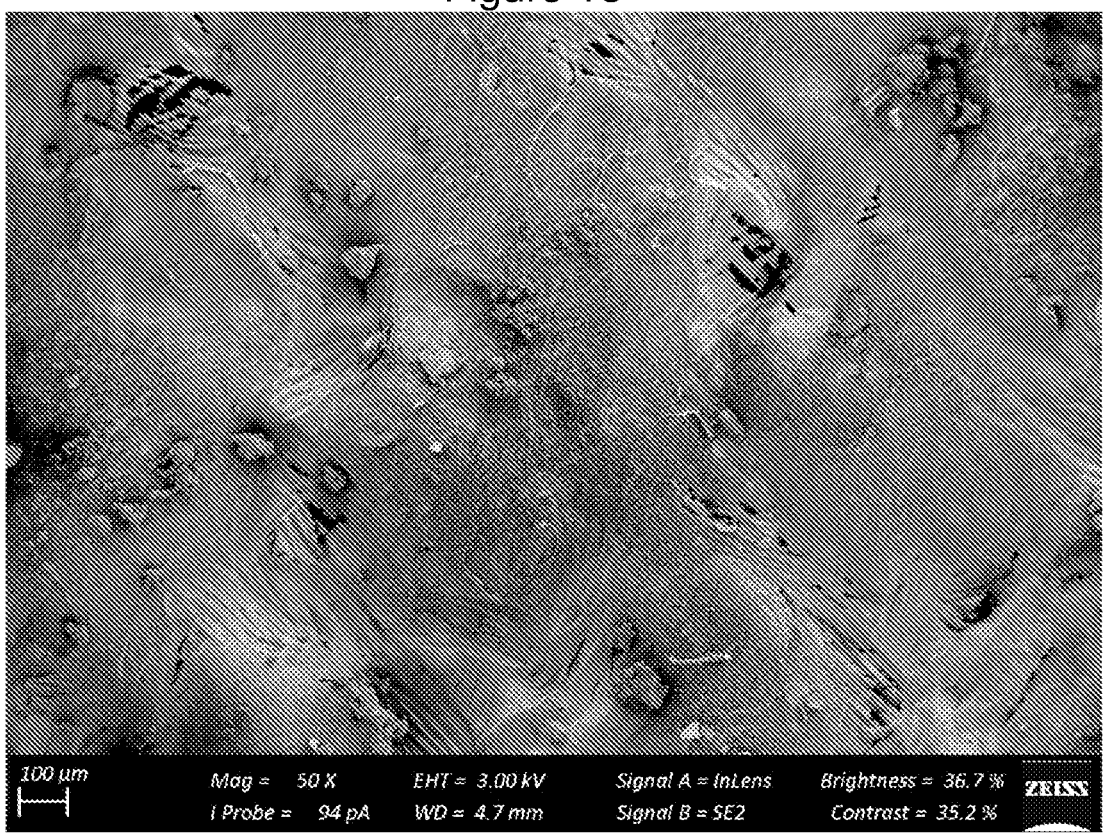
FIG. 19 is a further SEM micrograph of the cosmetic component in FIG. 13 after pressing showing hyaluronate powder particles in multiple regions of cold fusion in the nanofiber material layer.

At this point one, or both, of the substrate layers may be removed from the nanofiber sheets. In this example the substrate layer was removed from only one side. FIG. 17 is a SEM micrograph of part of one side of the product after cold pressing with the substrate removed from the nanofiber sheet. FIGS. 18 and 19 are SEM micrographs of the interior of the layers showing hyaluronate powder in regions of cold flow in the nanofiber material layer (and in regions where no bonding took place).

After pressing the nanofiber layers were no longer able to be separated without damaging them.

The panel was then further processed as follows:

Individual oval components of 7.5×5.0 cm were cut from the panel with a cutting die having a plurality of stainless steel oval blades and used on a Tippmann motorized roller cutter shimmed with a cutting board of 2 mm thickness. After cutting, the individual cosmetic components were gently removed from the die.

Example 3

An example of a cosmetic component was prepared as follows. An aqueous blended polymer solution containing Pullulan (average molecular weight 200 kDa), polyethylene oxide (average molecular weight 250 kDa), polysorbate 80, and Sodium Hyaluronate (average molecular weight between 10-35 kDa, and most preferably between 10-15 kDa) was prepared in the ratio of 73.3/13.3/8.3/5 wt % (based on the dry polymer loading), where the concentration in solution was 13.6/2.5/1.5/0.9 wt % respectively.

Proprietary SNC BEST™ technology was used to electrospin the fibers, from the resulting solution blend, to a planar density range within 1.7-3.2 gsm and an average fiber diameter range of 200-250 nm onto a substrate layer of polyester hexagonal netting to produce a first sheet or layer, measuring approximately 1 m×5 m, on substrate, where the substrate layer has a planar density of 38 gsm and a wire diameter of 185 µm, but any suitable substrate layer may be used.

Figure 20:
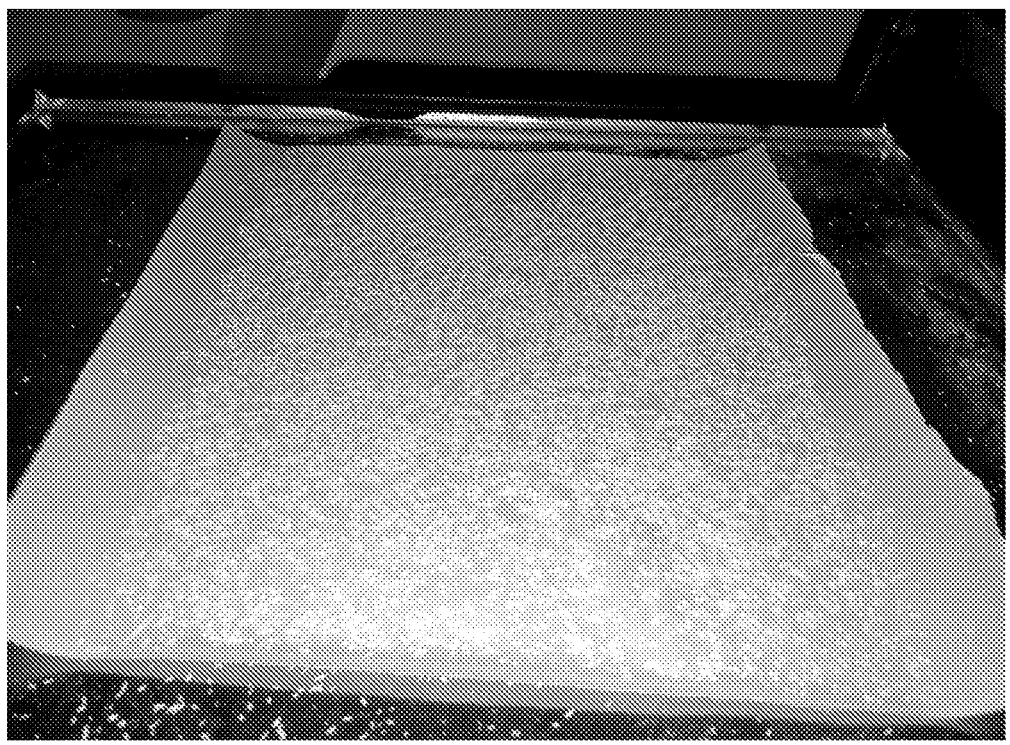
FIG. 20 is a photograph of a cosmetic component showing Pullulan powder distributed across a nanofiber layer.

Pullulan (average molecular weight 200 kDa) was then dispersed uniformly onto the surface of the first sheet or layer, nanofiber side up, until a dosage between 3-4 mg/cm$^2$, and most preferably between 3.3-3.5 mg/cm$^2$, was achieved to form a layer. This is illustrated in FIG. 20.

A second nanofiber sheet or layer of the same material and properties as the first, and also spun onto a substrate is then placed nanofiber side down on top of the Pullulan layer.

The resulting stacked layers, providing a layered or sandwich structure was then consolidated by pressing the entirety of the structure. To achieve this a 1.5 mm stainless steel 316/304 shim was placed on top of the layered structure which was then passed through a Keip Bros etching press at setting 2.5-3.5 at ambient environmental conditions. This setting was determined experimentally.

A large bonded panel results with a nanofiber-nanofiber bonding surface area of approximately 100% and a substrate-nanofiber bonding surface area of 14-34%.

Figure 21:
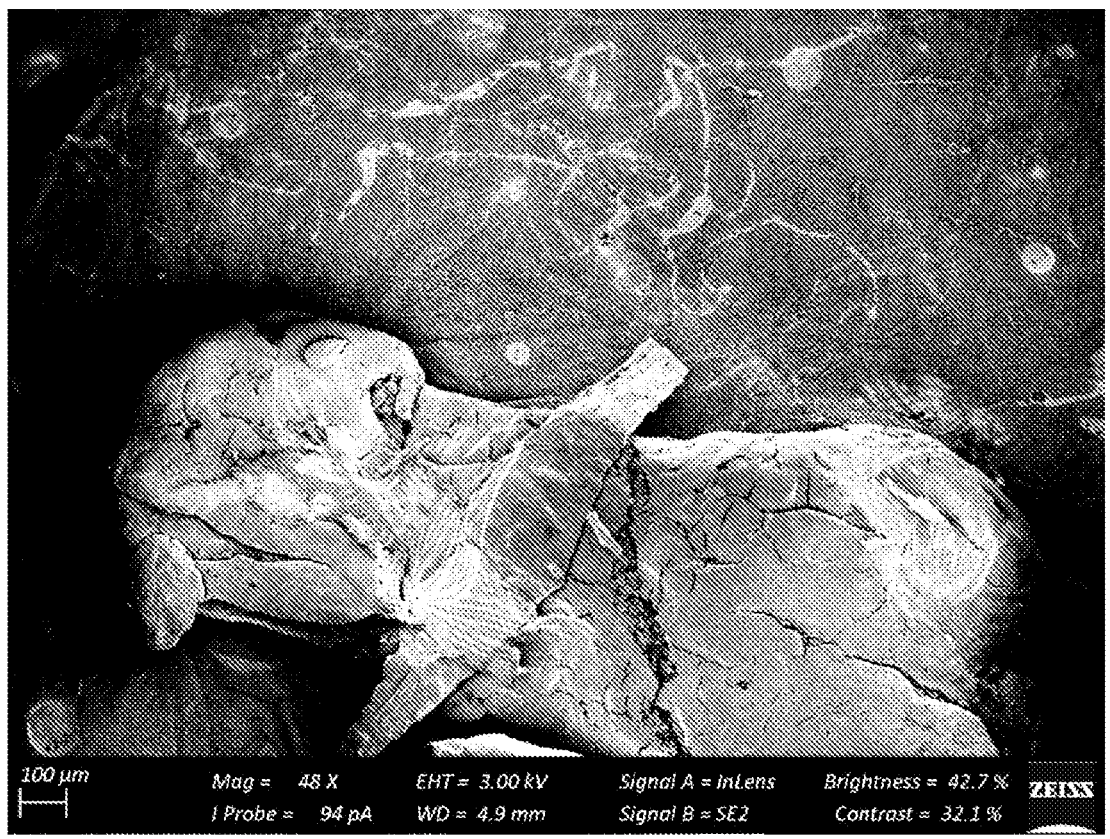
FIG. 21 is a SEM micrograph of the cosmetic component in FIG. 20 after being subjected to pressure and showing an impression from the mesh substrate on a Pullulan particle and adjacent nanofibers.

FIG. 21 is a SEM micrograph of a Pullulan particle between the nanofiber layers and shows an impression from the mesh substrate on a Pullulan particle and adjacent nanofibers. It can be seen that the Pullulan particle did not interfere with the cold flow of the nanofibers.

Figure 22:
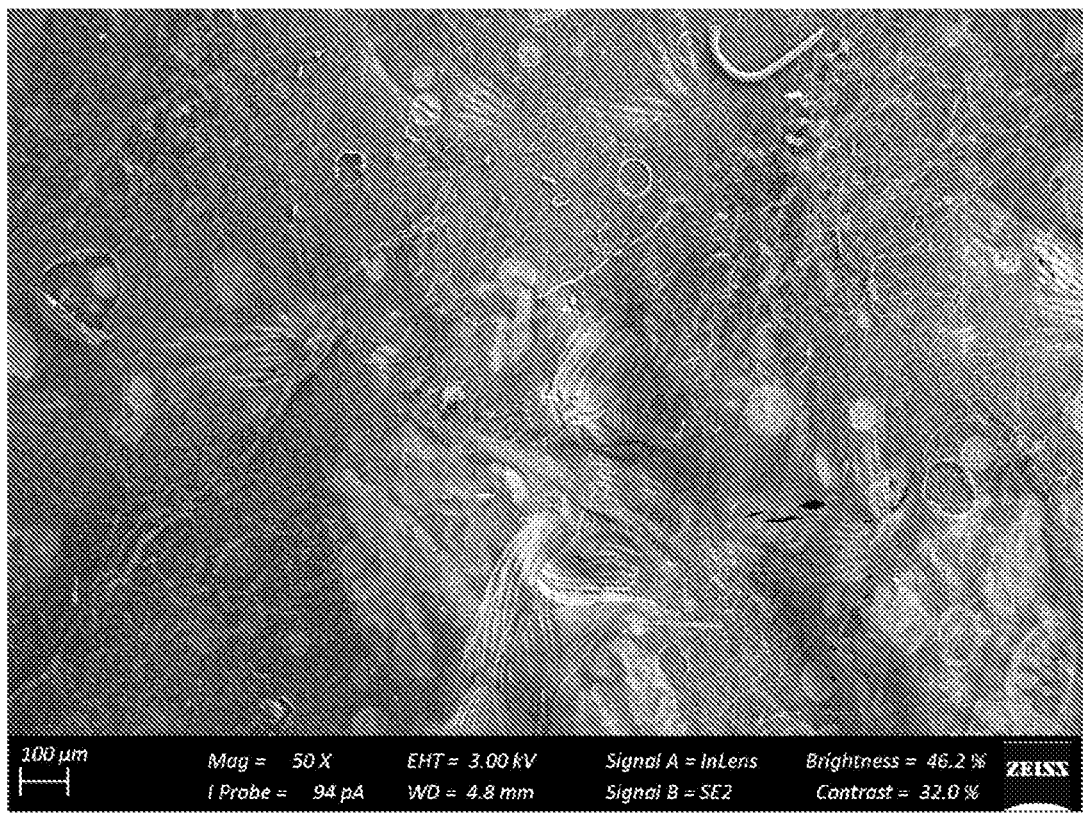
FIG. 22 is a further SEM micrograph of the cosmetic component in FIG. 20 after being subjected to pressure and showing an impression caused by a large Pullulan particle as a light region of nanofibers.

At this point one, or both, of the substrate layers may be removed from the nanofiber sheets. In this example the substrate layer was removed from only one side. FIG. 22 is a SEM micrograph of part of one side of the product after cold pressing with the substrate removed from the nanofiber sheet. An impression caused by a large Pullulan particle can be observed as a light region of nanofiber material.

Figure 23:
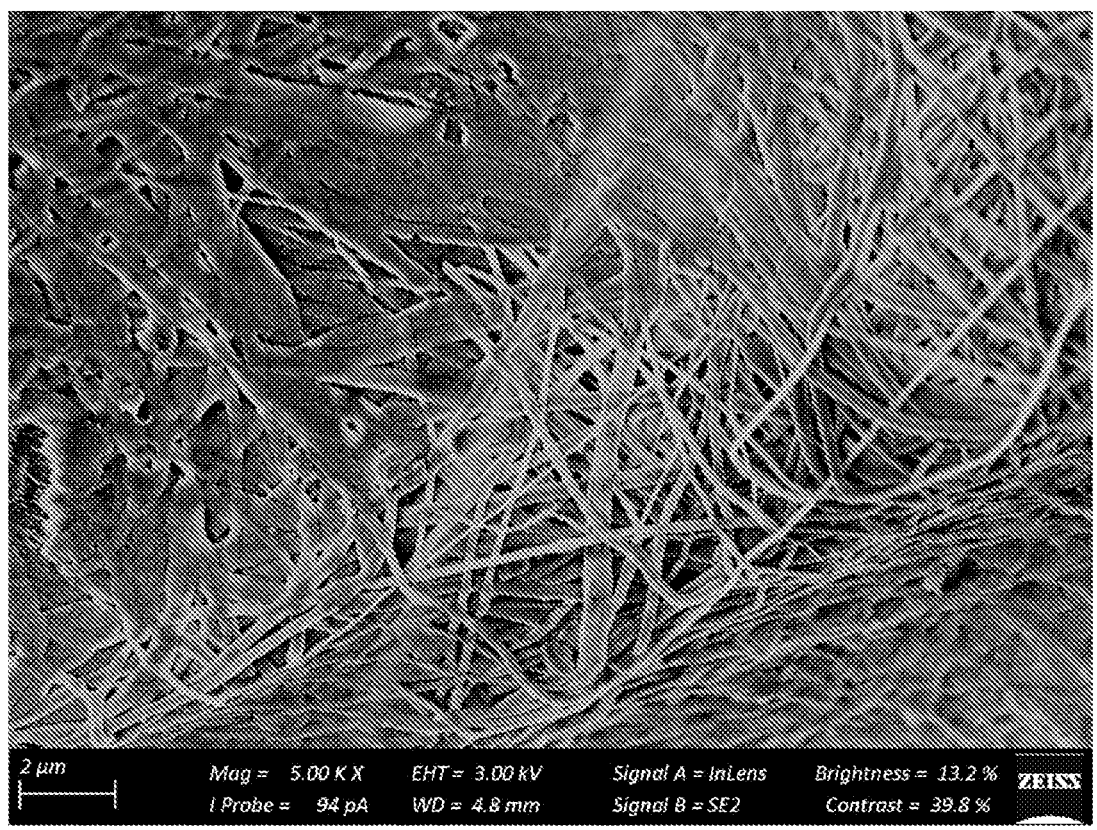
FIG. 23 is a SEM micrograph of the cosmetic component in FIG. 20 after pressing showing an interface between cold fused nanofibers and normal nanofibers.

FIG. 23 is a SEM micrograph of one of the nanofiber sheets showing an interface between cold fused nanofibers and normal nanofibers.

After pressing the nanofiber layers were no longer able to be separated without damaging them.

The panel was then further processed as follows:

Individual oval components of 7.5×5.0 cm were cut from the panel with a cutting die having a plurality of stainless steel oval blades and used on a Tippmann motorized roller cutter shimmed with a cutting board of 2 mm thickness. After cutting, the individual cosmetic components were gently removed from the die.

The current method avoids compatibility issues by dry cold pressing with no heat or liquid involved in the process. It further allows fixed loading of actives as these can be spread evenly and fixed in position. The method also permits a higher load limit of actives than what can be loaded into the fibers alone.

The foregoing description has been presented for the purpose of illustration; it is not intended to be exhaustive or to limit the invention to the precise forms disclosed. Persons skilled in the relevant art can appreciate that many modifications and variations are possible in light of the above disclosure.

The language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

Finally, throughout the specification and claims unless the contents requires otherwise the word 'comprise' or variations such as 'comprises' or 'comprising' will be understood to imply the inclusion of a stated integer or group of integers but not the exclusion of any other integer or group of integers.

The invention claimed is:

1. A method for preparing a cosmetic component which includes the steps of applying a layer of a dry cosmetic ingredient between a pair of fibrous sheets obtained by electrospinning one or more polymeric materials at least one of which is capable of cold flow under pressure, and characterised in that the layers of fibrous sheets are subjected to sufficient pressure over their surfaces to cause cold flow of at least some of the polymeric material such that at least parts of the fibrous sheets bond with each other and entrap the cosmetic ingredient in position between them.

2. The method as claimed in claim 1 in which the layer of a dry cosmetic ingredient is uniformly applied between the fibrous sheets.

3. The method as claimed in claim 1 in which pressure is applied in a patterned arrangement over the surface of the fibrous sheets to form a plurality of pockets in which the cosmetic ingredient is trapped and which prevent substantial migration of the cosmetic ingredients during further processing or handling.

4. The method as claimed in claim 1 in which pressure is applied over the entire surface of the fibrous sheets.

5. The method as claimed in claim 1 in which the cosmetic component is removed from a larger panel of material.

6. The method as claimed in claim 1 in which an ambient temperature during the method may be maintained between 1° C. to 35° C.

7. The method as claimed in claim 1 in which the polymeric material of the fibrous sheets is selected from thermoplastic polymers, or polymer blends containing thermoplastic polymers with an amorphous component that can be deformed.

8. The method as claimed in claim 7 in which the polymeric material is water soluble.

9. The method as claimed in claim 7 in which the polymeric material is one or more of polyethylene oxide (PEO), polyvinyl pyrrolidone (PVP), polyethylene glycol (PEG), polyvinyl acetate (PVAc), polyvinyl alcohol (PVOH).

10. The method as claimed in claim 1 in which either or both of the fibrous sheets are carried on a backing.

11. A cosmetic component which includes two layers of fibrous sheets obtained by electrospinning one or more polymeric materials, with a dry cosmetic component between the two layers, characterised in that the layers are secured together in at least one area of bonding created through cold flow of at least some of the polymeric material, which bonded area includes the dry cosmetic component.

12. The cosmetic component as claimed in claim 11 in which the at least one area of bonding extends over an entire surface of the cosmetic component.

13. The cosmetic component as claimed in claim 11 in which a plurality of areas of bonding extend over a surface of the cosmetic component, the plurality of areas of bonding defining a plurality of pockets between the two layers of fibrous sheets in which the cosmetic component is trapped.

14. The cosmetic component as claimed in claim 11 in which fiber forming components of at least one of the fibrous sheets have a glass transition temperature at standard room operating temperatures.

15. The cosmetic component as claimed in claim 11 in which cosmetic component may be impregnated with a cosmetic liquid.

* * * * *